(12) United States Patent
Ogbourne et al.

(10) Patent No.: US 10,143,638 B2
(45) Date of Patent: Dec. 4, 2018

(54) METHOD OF TREATING SKIN WITH INGENOL MEBUTATE

(75) Inventors: Steven Martin Ogbourne, Pinbarren (AU); David Thomas, Cardiff (GB); Ryan Moseley, Maested (GB); James Harrison Aylward, Indooroopilly (AU)

(73) Assignee: LEO Laboratories Limited, Dublin (IE)

( * ) Notice: Subject to any disclaimer, the term of this patent is extended or adjusted under 35 U.S.C. 154(b) by 598 days.

(21) Appl. No.: 13/201,331

(22) PCT Filed: Feb. 12, 2010

(86) PCT No.: PCT/AU2010/000152
§ 371 (c)(1),
(2), (4) Date: Oct. 19, 2011

(87) PCT Pub. No.: WO2010/091472
PCT Pub. Date: Aug. 19, 2010

(65) Prior Publication Data
US 2012/0041064 A1   Feb. 16, 2012

Related U.S. Application Data

(60) Provisional application No. 61/152,599, filed on Feb. 13, 2009.

(51) Int. Cl.
| | |
|---|---|
| *A61K 31/22* | (2006.01) |
| *A61P 17/00* | (2006.01) |
| *A61K 31/12* | (2006.01) |
| *A61K 8/37* | (2006.01) |
| *A61Q 19/08* | (2006.01) |
| *A61Q 17/04* | (2006.01) |

(52) U.S. Cl.
CPC .............. *A61K 8/375* (2013.01); *A61Q 19/08* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 8,653,133 B2* | 2/2014 | Ogbourne | C07C 67/52 514/511 |
| 2001/0051644 A1 | 12/2001 | Aylward | |
| 2007/0224150 A1* | 9/2007 | Chung | A61K 8/64 424/70.14 |
| 2008/0279885 A1 | 11/2008 | Mrue | |

FOREIGN PATENT DOCUMENTS

| | | |
|---|---|---|
| JP | 08-176004 | 7/1996 |
| JP | 2002-179581 | 6/2002 |
| JP | 2003-212781 | 7/2003 |
| WO | WO-2007-059584 | 5/2007 |
| WO | WO-2008-131491 | 11/2008 |

OTHER PUBLICATIONS

Peters & Foster (Drugs & Aging Apr. 1999, vol. 14, Issue 4, pp. 313-319).*
Machine Translation of JP 2003-212781 A (JP '781) 2003.*
Suzuki et al. (Biochem. J. (1995) 307, 817-821).*
Siller et al., "PEP005 (ingenol mebutate) gel, a novel agent for the treatment of actinic keratosis: results of a randomised, double-blind, vehicle-controlled, multicentre, phase IIa study." Australasian Journal of Dermatology, 2009 (published online Jan. 19, 2009), vol. 50, pp. 16-22.
International Search Report and Written Opinion dated Apr. 16, 2010, in corresponding PCT Application No. PCT/AU2010/000152.

* cited by examiner

*Primary Examiner* — Kortney L. Klinkel
*Assistant Examiner* — William Y Lee
(74) *Attorney, Agent, or Firm* — Finnegan, Henderson, Farabow, Garrett & Dunner LLP

(57) ABSTRACT

The present invention relates generally to the cosmetic treatment of aged skin. More specifically, the invention relates to the use of ingenol compounds, particularly ingenol angelates, in treating photo-aged and/or chronologically-aged skin.

39 Claims, 12 Drawing Sheets

A

B

C

D

E

F

A

B

C

D

E

F

A

B

C

D

E

F

A

B

C

D

E

F

A

B

A

B

A

B

METHOD OF TREATING SKIN WITH INGENOL MEBUTATE

CROSS-REFERENCE TO RELATED APPLICATIONS

This application claims the benefit of U.S. Provisional Application No. 61/152,599 filed on Feb. 13, 2009.

FIELD OF THE INVENTION

The present invention relates generally to the cosmetic treatment of aged skin. More specifically, the invention relates to the use of ingenol compounds, particularly ingenol angelates, in treating photo-aged and/or chronologically-aged skin.

BACKGROUND TO THE INVENTION

The reference in this specification to any prior publication (or information derived from it), or to any matter which is known, is not, and should not be taken as an acknowledgment or admission or any form of suggestion that prior publication (or information derived from it) or known matter forms part of the common general knowledge in the field of endeavour to which this specification relates.

Skin ageing is a dynamic process which is effected not only by intrinsic cellular and extracellular alterations over the passage of time but also by environmental, or extrinsic, factors such as inadequate nutrition, smoking, excessive alcohol consumption and particularly, chronic exposure to UV radiation.

Intrinsic, or chronological cutaneous aging is the result of inherent degeneration of connective tissue of the dermis. This form of skin aging is inevitable, although genetic influences may retard its onset and/or clinical progression. Instrinsically aged skin is manifested by epidermal and dermal atrophy, flattening of the epidermal rete ridge as well as decreased numbers of fibroblasts and mast cells and decreased levels of collagen. This is cosmetically characterized by a generally unblemished appearance but with fine lines, creases and loss of elasticity. (Baumann, L, 2007; Helfrich, Y. R, 2008; and references cited therein).

Photo-aging, a common causative factor in extrinsic aging, is the term used to describe the cosmetic and physiological effects of long-term exposure of the skin to environmental or artificial UV radiation. Whilst photo-aging can occur on any part of the body which is exposed to UV radiation, it occurs most commonly on the face, arms, hands, neck and upper chest. Photo-aged skin is manifested by an increase in the epidermal thickness or epidermal atrophy and most notably by solar elastosis, the accumulation of elastin-containing material just below the dermal-epidermal junction. Collagen and elastic fibres become fragmented and disorganized. At a cosmetic level this can be observed as a reddening and/or thickening of the skin (resulting in a leathery appearance), skin fragility and irregular pigmentation, loss of tone and elasticity (Baumann, L, 2007; Helfrich, Y. R, 2008; and references cited therein) as well as wrinkling, dryness, sunspots and deep furrow formation.

Hyaluronan, or hyaluronic acid (HA), is a high molecular weight ($1\times10^4$-$1\times10^7$ Da) non-sulfated polysaccharide component of the glycosaminoglycan family and is an important component of the dermal extracellular matrix (ECM), performing many pivotal structural and physiological functions. It consists of repeating disaccharide units of the sugars N-acetylglucosamine and D-glucuronic acid and is synthesized by HA synthase enzymes (HAS) of which three vertebrate genes have been isolated and characterized as HAS1, HAS2, and HAS3. Hyaluronan can bind up to 1000 times its weight in water and, together with other glycosaminoglycans (GAGs) helps the skin retain and maintain water, thereby maintaining a smooth, plump appearance. It is found in both the dermis and epidermis, particularly epidermal intercellular spaces, and is produced mainly by fibroblasts and keratinocytes.

Embryonic/early gestational foetal skin, the archetypical non-chronologically-aged/non-photo-aged skin, is characterized by elevated hyaluronan levels. In foetal skin it enhances collagen lattice reorganization and enhances the synthesis of collagen types III and V and in young skin, hyaluronan is found at the periphery of collagen and elastin fibres and where these intersect. In contrast, aged skin is characterized by de creased levels of hyaluronan and photo-aged skin has also been observed to exhibit reduced levels of hyaluronan. (Baumann, L., 2007 and references cited therein).

The increased hyaluronan levels associated with non-chronologically-aged/non-photo-aged skin, has been attributed to increased hyaluronan synthase (HAS) gene expression. It is commonly accepted that three HAS genes are responsible for the regulation of hyaluronan synthase; HAS1, HAS2 and HAS3. HAS1 gene expression is absent from non-aged/non-photo-aged fibroblasts. HAS2 is recognized as being essential to embryonic/foetal development and HAS3 is associated with chronologically-aged/photo-aged skin.

Hyaluronan molecular weight (in conjunction with concentration), is also important in influencing skin architecture, with high molecular weight hyaluronan forming a more effective pericellular coat than low molecular weight hyaluronan (Meran et al, 2007, 2008; Stern and Maibach, 2008). Indeed, the molecular weight of newly-synthesized hyaluronan in human skin is of high molecular weight, in both the epidermis and dermis. Whilst HAS1 and HAS3 are associated with the synthesis of lower molecular weight hyaluronan and as described above are associated with aged/photo-aged skin, HAS2-derived hyaluronan is of high molecular weight (typically at least $1.5\times10^6$ Da).

Although it is widely acknowledged that the best and most effective way of preventing, or at least minimizing, the photo-aging process is avoidance of exposure of the skin to UV radiation, namely staying out of the sun and wearing protective clothing and sunscreen, the intrinsic aging process is inevitable and there nevertheless remains a strong demand in today's youth-obsessed society for treatments which can "turn back the clock" by reversing or at least improving or ameliorating one or more of the cosmetic manifestations of the chronological-aging and/or photo-aging process such as lines, wrinkles, dryness, furrows, reddening, thickening, sunspots, loss of tone and elasticity, fragility, and irregular pigmentation. Indeed, consumer demand for cosmetic agents which can restore a youthful appearance to chronologically-aged or photo-aged skin, particularly facial skin, is ever increasing, with the anti-aging market expected to reach over $16.5 billion in sales by 2010 in the United States alone (Helfrich, Y. R., et al, 2008).

Given this demand, there remains a need for new treatments which may assist in reversing, improving or otherwise ameliorating one or more of the cosmetic manifestations associated with chronological-aging and photo-aging of skin.

SUMMARY OF THE INVENTION

The present invention is predicated on the finding that ingenol-3-angelate, an ingenol compound found in *Euphor-*

*bia* species, induces endogenous high molecular weight hyaluranon synthesis in dermal fibroblasts. Thus, there is provided a method of improving the cosmetic appearance of skin, in particular chronologically- or photo-aged skin.

Accordingly, in a first aspect, the present invention provides a method for the treatment of chronologically-aged and/or photo-aged skin in a subject comprising administering to the skin of said subject an ingenol compound or a pharmaceutically acceptable salt thereof.

In further aspects, the invention also provides ingenol compounds or their pharmaceutically acceptable salts, as well as compositions comprising a pharmaceutically acceptable carrier and said compounds or salts for use in the treatment of chronologically-aged and/or photo-aged skin. There is also provided the use of ingenol compounds, or their pharmaceutically acceptable salts in the manufacture of a composition or medicament for the treatment of chronologically-aged and/or photo-aged skin.

In another aspect, there is provided a method of inducing endogenous synthesis of hyaluronan in a subject comprising administering to the skin of said subject an ingenol compound or a pharmaceutically acceptable salt thereof.

A further aspect of the invention provides the use of an ingenol compound or a pharmaceutically acceptable salt thereof for inducing endogenous synthesis of hyaluronan in a subject.

Yet another aspect provides the use of an ingenol compound or a pharmaceutically acceptable salt thereof in the manufacture of a medicament for inducing endogenous synthesis of hyaluronan in a subject.

In some embodiments of the invention, the ingenol compound is administered topically to the skin.

In certain embodiments of the invention, the compound is selected from ingenol-3-angelate, 20-O-acetyl-ingenol-3-angelate and 20-deoxy-ingenol-3-angelate and, pharmaceutically acceptable salts and prodrugs thereof. In one example, the compound is ingenol-3-angelate or a pharmaceutically acceptable salt thereof.

DETAILED DESCRIPTION OF THE INVENTION

Figure 1A:
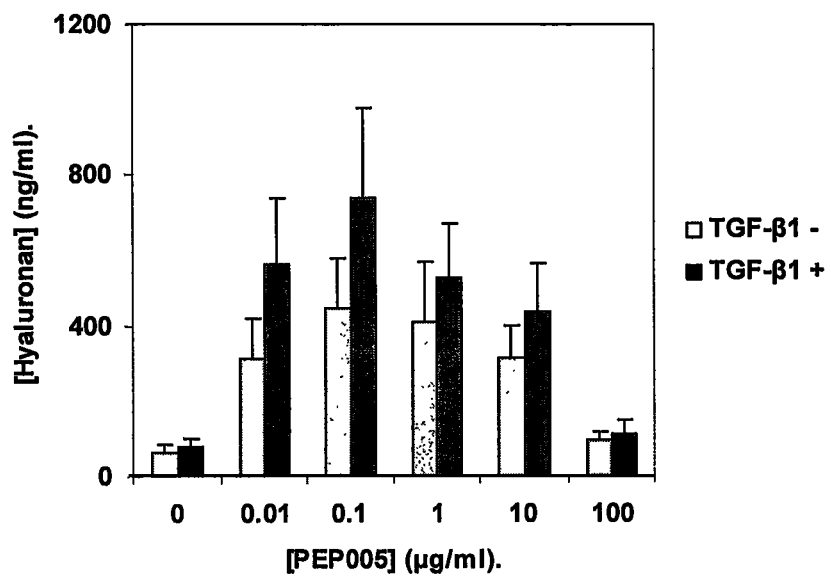
FIG. 1 graphically depicts average hyaluronan synthesis, by dermal fibroblasts, cultured in 0 µg/ml, 0.01 µg/ml, 0.1 µg/ml, 1 µg/ml, 10 µg/ml or 100 µg/ml PEP005, in the absence and presence of TGF-$\beta_1$ (10 ng/ml), at (A) 24 h and (B) 72 h, (N=3, average±SE, *p<0.05, p<0.01 and *p<0.001, compared to PEP005-free, dermal fibroblast-controls).

The singular forms "a", "an" and "the" include plural aspects unless the context clearly dictates otherwise. Thus, for example, reference to "an angeloyl substituted ingenane" or "an ingenol angelate" includes a single compound, as well as two or more compounds as appropriate.

Throughout this specification and the claims which follow, unless the context requires otherwise, the word "comprise" and variations such as "comprises" and "comprising" will be understood to imply the inclusion of a stated integer or step or group of integers but not the exclusion of any other integer or step or group of integers.

As used herein "treatment" is intended to refer to an improvement, full or partial restoration, or at least some reversal in the aesthetic or cosmetic appearance and/or physiological properties (such as increased hyaluranon presence) of the skin. Cosmetically, this may include the reduction, elimination, amelioration or otherwise improvement in appearance of one or more of dryness, fine lines, wrinkles, furrows, redness, sunspots and irregular pigmentation.

This may be assessed or determined by any means commonly used in the art. An exemplary method utilizes TruVu® Photography as described herein. Other methods may include the measurement or assessment of wrinkles in accordance with art known methods.

Reference to "high molecular weight hyaluronan" refers to a molecular weight value of at least about $1.5 \times 10^6$ Da. Molecular weight values may be determined in accordance with art known methods such as Gel Filtration Chromatography against known standards, see for example, Simpson, R. M., et al. 2009.

Reference to an "ingenol" includes compounds having the C3, C4, C5-trioxy trans bicyclo[4.4.1]-undecane ingenane skeleton. Such compounds are extensively reported and known in the literature and can be isolated from plants such as from a species of the family Euphorbiaceae or fully or partially chemically synthesized (see for example Winkler et al, 2002, and Tanino et al, 2003). Synthetically prepared ingenol compounds may include stereoisomers of naturally occurring ingenols. Thus racemates and stereoisomeric mixtures are also contemplated herein. The compounds contemplated herein are generally found in extracts of the Euphorbiaceae plants. An extract may comprise, therefore, sap or liquid or semi-liquid material exuded from, or present in, leaves, stem, flowers, seeds, bark or between the bark and the stem. Most preferably, the extract is from sap. Furthermore, the extract may comprise liquid or semi-liquid material located in fractions extracted from sap, leaves, stems, flowers, bark or other plant material of the Euphoriaceae plant. For example, plant material may be subject to physical manipulation to disrupt plant fibres and extracellular matrix material and inter- and intra-tissue extracted into a solvent including an aqueous environment. All such sources of the compounds are encompassed by the present invention including compounds obtained by chemically synthetic routes. In certain embodiments of the invention, the ingenol compound is used in isolated or purified form, meaning that it is or has been made substantially free or devoid of other compounds or contaminating agents from the natural source or isolation or synthetic process. It will be recognized however, that the purified form may then be subsequently mixed or formulated with further compounds, including those from the natural source, if desired. In certain embodiments the substantially purified ingenol compound is at least 95% pure. In other embodiments the substantially purified compound is at least 97 or 98% pure. In yet other embodiments the substantially purified compound is at least 99 or 99.5% pure.

Reference herein to a member of the Euphorbiaceae family includes reference to species from the genera *Acalypha, Acidoton, Actinostemon, Adelia, Adenocline, Adenocrepis, Adenophaedra, Adisca, Agrostistachys, Alchornea, Alchorneopsis, Alcinaeanthus, Alcoceria, Aleurites, Amanoa, Andrachne, Angostyles, Anisophyllum, Antidesma, Aphora, Aporosa, Aporosella, Argythamnia, Astrococcus, Astrogyne, Baccanrea, Baliospermum, Bernardia, Beyeriopsis, Bischofia, Blachia, Blumeodondron, Bonania, Bradleia, Breynia, Breyniopsis, Briedelia, Buraeavia, Caperonia, Caryodendron, Celianella, Cephalocroton, Chaenotheca, Chaetocarpus, Chamaesyce, Cheilosa, Chiropetalum, Choriophyllum, Cicca, Chaoxylon, Cleidon, Cleistanthus, Cluytia, Cnesmone, Cnidoscolus, Coccoceras, Codiaeum, Coelodiscus, Conami, Conceveiba, Conceveibastrum, Concevelbum, Corythea, Croizatia, Croton, Crotonopsis, Crozophora, Cubanthus, Cunuria, Dactylostemon, Dalechampia, Dendrocousinsia, Diaspersus, Didymocistus, Dimorphocalyx, Discocarpus, Ditaxis, Dodecastigma, Drypetes, Dysopsis, Elateriospermum, Endadenium, Endospermum, Erismanthus, Erythrocarpus, Erythrochilus, Eumecanthus, Euphorbia, Euphorbiodendron, Excoecaria, Flueggea, Calearia, Garcia, Gavarretia, Gelonium, Giara, Givotia, Glochidion, Clochidionopsis, Glycyclendron, Gymnanthes, Gymnosparia, Haematospermum, Hendecandra, Hevea, Hieronima, Hieronyma, Hippocrepandra, Homalanthus, Hymenocardia, Janipha, Jatropha, Julocroton, Lasiocroton, Leiocarpus, Leonardia, Lepidanthus, Leucocroton, Mabea, Macaranga, Mallotus, Manihot, Mappa, Maprounea, Melanthesa, Mercurialis, Mettenia, Micrandra, Microdesmis, Microelus, Microstachy, Maocroton, Monadenium, Mozinna, Neoscortechinia, Omalanthus, Omphalea, Ophellantha, Orbicularia, Ostodes, Oxydectes, Palenga, Pantadenia, Paradrypeptes, Pausandra, Pedilanthus, Pera, Peridium, Petalostigma, Phyllanthus, Picrodendro, Pierardia, Pilinophytum, Pimeleodendron, Piranhea, Platygyna, Plukenetia, Podocalyx, Poinsettia, Poraresia, Prosartema, Pseudanthus, Pycnocoma, Quadrasia, Reverchonia, Richeria, Richeriella, Ricinella, Ricinocarpus, Rottlera, Sagotia, Sanwithia, Sapium, Savia, Sclerocroton, Sebastiana, Securinega, Senefeldera, Senefilderopsis, Serophyton, Siphonia, Spathiostemon, Spixia, Stillingia, Strophioblachia, Synadenium, Tetracoccus, Tetraplandra, Tetrorchidium, Thyrsanthera, Tithymalus, Trageia, Trewia, Trigonostemon, Tyria* and *Xylophylla*.

A preferred genus and particularly suitable for the practice of the present invention is the genus *Euphorbia*. Particularly useful species of this genus include *Euphorbia aaron-rossii, Euphorbia abbreviata, Euphorbia acuta, Euphorbia alatocaulis, Euphorbia albicaulis, Euphorbia algomarginata, Euphorbia aliceae, Euphorbia altai, Euphorbia anacampseros, Euphorbia andromedae, Euphorbia angusta, Euphorbia anthonyi, Euphorbia antiguensis, Euphorbia apocynifolia, Euphorbia arabica, Euphorbia ariensis, Euphorbia arizonica, Euphorbia arkansana, Euphorbia arteagae, Euphorbia arundelana, Euphorbia astroites, Euphorbia atrococca, Euphorbia baselicis, Euphorbia batabanensis, Euphorbia bergeri, Euphorbia bermudiana, Euphorbia bicolor, Euphorbia biformis, Euphorbia bifurcata, Euphorbia bilobata, Euphorbia biramensis, Euphorbia biuncialis, Euphorbia blepharostipula, Euphorbia blodgetti, Euphorbia boerhaavioides, Euphorbia boliviana, Euphorbia bracei, Euphorbia brachiata, Euphorbia brachycera, Euphorbia brandegee, Euphorbia brittonii, Euphorbia caesia, Euphorbia calcicola, Euphorbia campestris, Euphorbia candelabrum, Euphorbia capitellata, Euphorbia carmenensis, Euphorbia carunculata, Euphorbia cayensis, Euphorbia celastroides, Euphorbia chalicophila, Euphorbia chamaerrhodos, Euphorbia chamaesula, Euphorbia chiapensis, Euphorbia chiogenoides, Euphorbia cinerascens, Euphorbia clarionensis, Euphorbia colimae, Euphorbia colorata, Euphorbia commutata, Euphorbia consoquitlae, Euphorbia convolvuloides, Euphorbia corallifera, Euphorbia creberrima, Euphorbia crenulata, Euphorbia cubensis, Euphorbia cuspidata, Euphorbia cymbiformis, Euphorbia darlingtonii, Euphorbia defoliata, Euphorbia degeneri, Euphorbia deltoidea, Euphorbia dentata, Euphorbia depressa Euphorbia dictyosperma, Euphorbia dioeca, Euphorbia discoidalis, Euphorbia dorsiventralis, Euphorbia drumondii, Euphorbia duclouxii, Euphorbia dussii, Euphorbia eanophylla, Euphorbia eggersii, Euphorbia eglandulosa, Euphorbia elata, Euphorbia enalla, Euphorbia eriogonoides, Euphorbia eriophylla, Euphorbia esculaeformis, Euphorbia espirituensis, Euphorbia esula, Euphorbia excisa, Euphorbia exclusa, Euphorbia exstipitata, Euphorbia exstipulata, Euphorbia fendleri, Euphorbia filicaulis, Euphorbia filiformis, Euphorbia florida, Euphorbia fruticulosa, Euphorbia garber, Euphorbia gaumerii, Euphorbia gerardiana, Euphorbia geyeri, Euphorbia glyptosperma, Euphorbia gorgonis, Euphorbia gracilior, Euphorbia gracillima, Euphorbia gradyi, Euphorbia graminea, Euphorbia graminiea Euphorbia grisea, Euphorbia guadalajarana, Euphorbia guanarensis, Euphorbia gymnadenia, Euphorbia haematantha, Euphorbia hedyotoides, Euphorbia heldrichii, Euphorbia helenae, Euphorbia helleri, Euphorbia helwigii, Euphorbia henricksonii, Euphorbia heterophylla, Euphorbia hexagona, Euphorbia hexagonoides, Euphorbia hinkleyorum, Euphorbia hintonii, Euphorbia hirtula, Euphorbia hirta, Euphorbia hooveri, Euphorbia humistrata, Euphorbia hypericifolia, Euphorbia inundata, Euphorbia*

*involuta, Euphorbia jaliscensis, Euphorbia jejuna, Euphorbia johnston, Euphorbia juttae, Euphorbia knuthii, Euphorbia lasiocarpa, Euphorbia lata, Euphorbia latazi, Euphorbia latericolor, Euphorbia laxiflora Euphorbia lecheoides, Euphorbia ledienii, Euphorbia leucophylla, Euphorbia lineata, Euphorbia linguiformis, Euphorbia longecornuta, Euphorbia longepetiolata, Euphorbia longeramosa, Euphorbia longinsulicola, Euphorbia longipila, Euphorbia lupulina, Euphorbia lurida, Euphorbia lycioides, Euphorbia macropodoides, Euphorbia macvaughiana, Euphorbia manca, Euphorbia mandoniana, Euphorbia mangleti, Euphorbia mango, Euphorbia marylandica, Euphorbia mayana, Euphorbia melanadenia, Euphorbia melanocarpa, Euphorbia meridensis, Euphorbia mertonii, Euphorbia mexiae, Euphorbia microcephala, Euphorbia microclada, Euphorbia micromera, Euphorbia misella, Euphorbia missurica, Euphorbia montana, Euphorbia montereyana, Euphorbia multicaulis, Euphorbia multiformis, Euphorbia multinodis, Euphorbia multiseta, Euphorbia muscicola, Euphorbia neomexicana, Euphorbia nephradenia, Euphorbia niqueroana, Euphorbia oaxacana, Euphorbia occidentalis, Euphorbia odontodenia, Euphorbia olivacea, Euphorbia olowaluana, Euphorbia opthalmica, Euphorbia ovata, Euphorbia pachypoda, Euphorbia pachyrhiza, Euphorbia padifolia, Euphorbia palmeri, Euphorbia paludicola, Euphorbia parciflora, Euphorbia parishii, Euphorbia parryi, Euphorbia paxiana, Euphorbia pediculifera, Euphorbia peplidion, Euphorbia peploides, Euphorbia peplus, Euphorbia pergamena, Euphorbia perlignea, Euphorbia petaloidea, Euphorbia petrina, Euphorbia picachensis, Euphorbia pilosula, Euphorbia pilulifera, Euphorbia pinariona, Euphorbia pinetorum, Euphorbia pionosperma, Euphorbia platysperma, Euphorbia plicata, Euphorbia poeppigii, Euphorbia poliosperma, Euphorbia polycarpa, Euphorbia polycnemoides, Euphorbia polyphylla, Euphorbia portoricensis, Euphorbia portulacoides Euphorbia portulana, Euphorbia preslii, Euphorbia prostrata, Euphorbia pteroneura, Euphorbia pycnanthema, Euphorbia ramosa, Euphorbia rapulum, Euphorbia remyi, Euphorbia retroscabra, Euphorbia revoluta, Euphorbia rivularis, Euphorbia robusta, Euphorbia romosa, Euphorbia rubida, Euphorbia rubrosperma, Euphorbia rupicola, Euphorbia sanmartensis, Euphorbia saxatilis M. Bieb, Euphorbia schizoloba, Euphorbia sclerocyathium, Euphorbia scopulorum, Euphorbia senilis, Euphorbia serpyllifolia, Euphorbia serrula, Euphorbia setiloba Engelm, Euphorbia sonorae, Euphorbia soobyi, Euphorbia sparsiflora, Euphorbia sphaerosperma, Euphorbia syphilitica, Euphorbia spruceana, Euphorbia subcoerulea, Euphorbia stellata, Euphorbia submammilaris, Euphorbia subpeltata, Euphorbia subpubens, Euphorbia subreniforme, Euphorbia subtrifoliata, Euphorbia succedanea, Euphorbia tamaulipasana, Euphorbia telephioides, Euphorbia tenuissima, Euphorbia tetrapora, Euphorbia tirucalli, Euphorbia tomentella, Euphorbia tomentosa, Euphorbia torralbasii, Euphorbia tovariensis, Euphorbia trachysperma, Euphorbia tricolor, Euphorbia troyana, Euphorbia tuerckheimii, Euphorbia turczaminowii, Euphorbia umbellulata, Euphorbia undulata, Euphorbia vermiformis, Euphorbia versicolor, Euphorbia villifera, Euphorbia violacea, Euphorbia whitei, Euphorbia xanti Engelm, Euphorbia xylopoda Greenm., Euphorbia yayalesia Urb., Euphorbia yungasensis, Euphorbia zerayschanica and Euphorbia zinniiflora.*

In some embodiments species of the genus *Synadenium* include *Synadenium grantii* and *Synadenium compactum*.

In some embodiments species of the genus *Monadenium* include *Monadenium lugardae* and *Monadenium guentheri*.

In one embodiment a species of the genus *Endadenium* is *Endadenium gossweileni*.

In another embodiment *Euphorbia peplus* is useful in the practice of the present invention in terms of providing a source of ingenol compounds such as ingenol angelates. Reference herein to "*Euphorbia peplus*" or its abbreviation "*E. peplus*" includes various varieties, strains, lines, hybrids or derivatives of this plant as well as its botanical or horticultural relatives. Furthermore, the present invention may be practiced using a whole Euphorbiaceae plant or parts thereof including sap or seeds or other reproductive material may be used. Generally, for seeds or reproductive material to be used, a plant or plantlet is first required to be propagated.

Reference herein to a Euphorbiaceae plant, a *Euphorbia* species or *E. peplus* further encompasses genetically modified plants. Genetically modified plants include trangenic plants or plants in which a trait has been removed or where an endogenous gene sequence has been down-regulated, mutated or otherwise altered including the alteration or introduction of genetic material which exhibits a regulatory effect on a particular gene. Consequently, a plant which exhibits a character not naturally present in a Euphorbiaceae plant or a species of *Euphorbia* or in *E. peplus* is nevertheless contemplated by the present invention and is included within the scope of the above-mentioned terms.

In one embodiment of the invention, the ingenol compound has the formula:

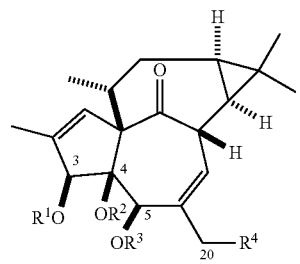

wherein
$R^1$-$R^3$ are independently selected from hydrogen, optionally substituted alkyl, optionally substituted alkenyl, optionally substituted alkynyl, optionally substituted acyl, optionally substituted aryl, optionally substituted arylalkyl, $S(O)_2R'$, $S(O)_2OR'$, $P(O)(OR')_2$ (wherein R' is hydrogen, alkyl, alkenyl, alkynyl, acyl, aryl, or arylalkyl) and glycosyl or $R^1$ and $R^2$ or $R^2$ and $R^3$ may form a methylene or ethylene chain; and
$R^4$ is selected from hydrogen, hydroxy, optionally substituted alkoxy, optionally substituted alkenoxy, optionally substituted alkynoxy, optionally substituted acyloxy, optionally substituted arylalkoxy, $OS(O)_2R'$, $OS(O)_2OR'$, $OP(O)(OR')_2$ (wherein R' is hydrogen, alkyl, alkenyl, alkynyl, acyl, aryl, or arylalkyl) and glycoxy.

In some examples, at least one of $R^1$-$R^4$ is not hydrogen. In a further example thereof, $R^1$ is not hydrogen.

In some examples of the invention, $R^1$ is an optionally substituted acyl group C(O)—R. In further examples thereof, R is optionally substituted alkyl, alkenyl or alkynyl. In further examples thereof, R may be straight chain or branched and may have up to 6 or up to 10 carbon atoms. In still further examples thereof, R is branched.

In certain examples of the invention, one of $R^1$-$R^3$ is an angeloyl group, as depicted by the formula (i) below, or $R^4$ is an O-angeloyl group. Such compounds are referred to herein as ingenol angelates. In one such examples of the invention, $R^1$ is an angeloyl group of formula (i).

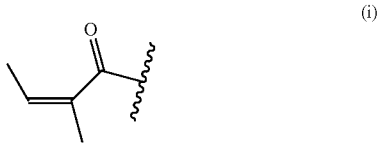 [SMILES: *C(=O)/C(C)=C\C]

(i)

In certain examples of the invention one or both of $R^2$ and $R^3$ are hydrogen. $R^2$ and $R^3$ together may also form a methylene or ethylene dioxy group.

In certain examples of the invention $R^4$ is hydrogen, hydroxy or acyloxy such as a group of the formula —OC(O)$C_{1-6}$alkyl, for example acetoxy.

In certain examples of the invention, compounds for use in the described methods, uses and compositions are ingenol-3-angelate, 20-O-acetyl-ingenol-3-angelate and 20-deoxy-ingenol-3-angelate (depicted below) and pharmaceutically acceptable salts and prodrugs thereof.

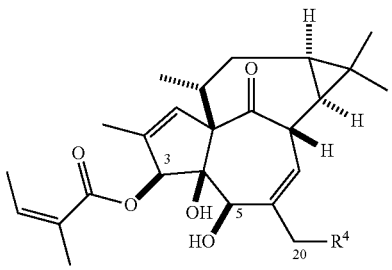

$R^4$ = OH, ingenol-3-angelate
$R^4$ = OAc, 20-O-Acetyl-ingenol-3-angelate
$R^4$ = H, 20-deoxy-ingenol-3-angelate In one embodiment of the present invention the compound is ingenol-3-angelate. Reference herein to "ingenol-3-angelate" includes naturally occurring as well as chemically synthetic forms.

Whilst it is recognized that the compounds may be used as the sap or extracts from Euphorbiacae, the ingenol compounds contemplated herein are advantageously used in at least partially purified or isolated form, such as at least 95% purified form, typically at least 97, 98 or 99% pure.

Alkylation, alkenylation, alkynylation, arylation, arylalkylation or acylation can be carried out on the ingenol compounds using methods known in the art of synthetic chemistry for alkylating, alkenylation, alkynylation, arylation, arylalkylating or acylating free hydroxy groups (see for example, Greene and Wutz, Protective Groups in Organic Synthesis, 1999; March, *Advanced Organic Chemistry*, 5th Edition; Larock, Comprehensive Organic Transformations, 1999; the entire contents of which are incorporated herein by reference). For example, hydroxy groups can be alkylated (or arylalkylated) using alkyl (or arylalkyl) halides, such as methyl iodide (or benzylbromide), or dialkyl sulfates, such as dimethyl or diethyl sulfate. Acylation can be effected by treatment with appropriate carboxylic acids, acid halides and acid anhydrides in the presence of a base or a coupling agent. Glycosidic formation may be effected chemically, for example, by reacting the ingenol compound with a protected sugar compound in which C-1 has been activated by halogenation for coupling with the hydroxyl or carboxyl groups and the sugar hydroxyl groups have been blocked by protecting groups. Alternatively, glycoside formation may be effected enzymatically using an appropriate glycosyltransferase such as UDP-galactose dependent galactocyltransferase and UDP-glucose dependent glycotransferase. Preferred C-1 linked saccharides area furanose or pyranose saccharide (sugar) substituent which is linked to the ingenol angelate structure through C-1 of the saccharide (conventional numbering) to form an acetyl linkage. Exemplary saccharide groups include reducing sugars such as glucose, ribose, arabinose, xylose, mannose and galactoses, each being linked to an oxygen atom of the ingenol compound.

Sulfate, sulfonate and phosphate groups can be prepared by methods known in the art. Examples of R' include hydrogen, $C_{1-6}$alkyl, phenyl and benzyl.

As used herein, the term "alkyl" denotes straight chain, or branched alkyl, preferably $C_{1-20}$ alkyl, e.g. $C_{1-10}$ or $C_{1-6}$. Examples of straight chain and branched alkyl include methyl, ethyl, n-propyl, isopropyl, n-butyl, sec-butyl, t-butyl, n-pentyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Where an alkyl group is referred to generally as "propyl", "butyl" etc, it will be understood that this can refer to any of straight, branched and cyclic isomers where appropriate. An alkyl group may be optionally substituted by one or more optional substituents as herein defined. A "cycloalkyl" group is a cyclic alkyl group of at least three carbon atoms, e.g. $C_3$-$C_8$, such as $C_3$, $C_4$, $C_5$ or $C_6$ cycloalkyl. Examples of "cycloalkyl" include mono- or polycyclic alkyl groups such as cyclopropyl, cyclobutyl, cyclopentyl, cyclohexyl, cycloheptyl, cyclooctyl, cyclononyl, cyclodecyl and the like. A cycloalkyl group may be optionally substituted by one or more optional substituents as herein defined.

The term "alkenyl" as used herein denotes groups formed from straight chain, branched or cyclic hydrocarbon residues containing at least one carbon to carbon double bond including ethylenically mono-, di- or poly-unsaturated alkyl or cycloalkyl groups as previously defined, preferably $C_{2-20}$ alkenyl (e.g. $C_{2-10}$ or $C_{2-6}$). Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4,pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl. An alkenyl group may be optionally substituted by one or more optional substituents as herein defined.

As used herein the term "alkynyl" denotes groups formed from straight chain, branched or cyclic hydrocarbon residues containing at least one carbon-carbon triple bond including ethynically mono-, di- or poly-unsaturated alkyl or cycloalkyl groups as previously defined. Unless the number of carbon atoms is specified the term preferably refers to $C_{2-20}$ alkynyl (e.g. $C_{2-10}$ or $C_{2-6}$). Examples include ethynyl, 1-propynyl, 2-propynyl, and butynyl isomers, and pentynyl isomers. An alkynyl group may be optionally substituted by one or more optional substitutents as herein defined.

The term "aryl" denotes any of single, polynuclear, conjugated and fused residues of aromatic hydrocarbon ring systems. Examples of aryl include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl. Preferred aryl include phenyl and naphthyl. An aryl group may be optionally substituted by one or more optional substituents as herein defined.

The term "acyl" denotes a group C(O)—R, wherein R can be a hydrogen, alkyl, cycloalkyl, alkenyl, alkynyl, arylalkyl or aryl residue. Examples of acyl include formyl, straight chain or branched alkanoyl (e.g. $C_{1-20}$) such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; straight chain or branched alkenoyl (e.g. $C_{2-20}$) such as angeloyl; and aroyl such as benzoyl, toluoyl and naphthoyl. The R residue may be optionally substituted as described herein.

An arylalkyl group is an alkyl group as defined herein, substituted by an aryl group as defined herein. In one embodiment, the alkyl group is terminally substituted by the aryl group. Examples of arylalkyl include phenyl$C_1$-$C_{20}$alkyl such as benzyl, phenylethyl, phenylpropyl, phenylbutyl, phenylpentyl and phenylhexyl. One or both of the alkyl and aryl groups may be independently optionally substituted by one or more optional substituents as described herein.

The term "optionally substituted" means that a group may be unsubstituted or substituted by one or more, same or different, substituents. Optional substituents for alkyl, alkenyl, alkynyl, aryl, arylalkyl, aryl, and thus acyl, include: halo (chloro, bromo, iodo and fluoro), hydroxy, $C_{1-6}$ alkoxy, $C_{1-6}$alkyl, $C_{3-6}$cycloalkyl, phenyl, nitro, halomethyl (e.g. tribromomethyl, trichloromethyl, trifluoromethyl), halomethoxy (e.g. trifluoromethoxy, tribromomethoxy), C(O)$C_{1-6}$alkyl, amino (NH$_2$), $C_{1-6}$alkylamino, (e.g. methylamino, ethylamino and propylamino) di$C_{1-6}$alkylamino (e.g. dimethylamino, diethylamino and dipropylamino), CO$_2$H, CO$_2$C$_{1-6}$ alkyl, thio (SH) and $C_{1-6}$alkylthio. An optional substituent also includes the replacement of a CH$_2$ group by a carbonyl (C=O) group or may be a methylene or ethylene dioxy group.

It will be recognized that during synthetic or semi-synthetic processes for the preparation of ingenol compounds contemplated by the present invention, it may be necessary or desirable to protect other functional groups which may be reactive or sensitive to the reaction or transformation conditions undertaken. Suitable protecting groups for such functional groups are known in the art and may be used in accordance with standard practice. As used herein, the term "protecting group", refers to an introduced functionality which temporarily renders a particular functional group inactive under the conditions to which the compound will be subjected. Such protecting groups and methods for their installation and subsequent removal at an appropriate stage are well known (Greene and Wutz, 1999 supra).

The present invention also relates to prodrugs of ingenol compounds for use as described herein. Any compound that is a prodrug of an ingenol compound is within the scope and spirit of the invention. The term "prodrug" is used in its broadest sense and encompasses those derivatives that are converted in vivo, either enzymatically or hydrolytically, to the compounds of the invention. Such derivatives would readily occur to those skilled in the art, and include, for example, compounds where a free thiol or hydroxy group is converted into an ester, such as an acetate, or thioester or where a free amino group is converted into an amide. Procedures for acylating the compounds of the invention, for example to prepare ester and amide prodrugs, are well known in the art and may include treatment of the compound with an appropriate carboxylic acid, anhydride or chloride in the presence of a suitable catalyst or base. Esters of carboxylic acid (carboxy) groups are also contemplated. Suitable esters $C_{1-6}$alkyl esters; $C_{1-6}$alkoxymethyl esters, for example methoxymethyl or ethoxymethyl; $C_{1-6}$alkanoyloxymethyl esters, for example, pivaloyloxymethyl; phthalidyl esters; $C_{3-8}$cycloalkoxycarbonyl$C_{1-6}$alkyl esters, for example, 1-cyclohexylcarbonyloxyethyl; 1,3-dioxolen-2-onylmethyl esters, for example, 5-methyl-1,3-dioxolen-2-onylmethyl; and $C_{1-6}$alkoxycarbonyloxyethyl esters, for example, 1-methoxycarbonyloxyethyl. Prodrugs of amino functional groups include amides (see, for example, *Adv. BioSci.*, 1979, 20, 369, Kyncl, J. et al), enamines (see, for example, *J. Pharm. Sci.*, 1971, 60, 1810, Caldwell, H. et al), Schiff bases (see, for example, U.S. Pat. No. 2,923,661 and *Antimicrob. Agents Chemother.*, 1981, 19, 1004, Smyth, R. et al), oxazolidines (see, for example, *J. Pharm. Sci*, 1983, 72, 1294, Johansen, M. et al), Mannich bases (see, for example, *J. Pharm. Sci.* 1980, 69, 44, Bundgaard, H. et al and *J. Am. Chem. Soc.*, 1959, 81, 1198, Gottstein, W. et al), hydroxymethyl derivatives (see, for example, *J. Pharm. Sci,* 1981, 70, 855, Bansal, P. et al) and N-(acyloxy)alkyl derivatives and carbamates (see, for example, *J. Med. Chem.,* 1980, 23, 469, Bodor, N. et al, *J. Med. Chem.*, 1984, 27, 1037, Firestone, R. et al, *J. Med. Chem.,* 1967, 10, 960, Kreiger, M. et al, U.S. Pat. No. 5,684,018 and *J. Med. Chem.,* 1988, 31, 318-322, Alexander, J. et al). Other conventional procedures for the selection and preparation of suitable prodrugs are known in the art and are described, for example, in WO 00/23419; *Design of Prodrugs*, H. Bundgaard, Ed., Elsevier Science Publishers, 1985; *Methods in Enzymology,* 42: 309-396, K. Widder, Ed, Academic Press, 1985; *A Textbook of Drug Design and Development*, Krogsgaard-Larsen and H. Bundgaard, Eds, Chapter 5, p 113-191 (1991); *Advanced Drug Delivery Reviews,* 8; 1-38 (1992); *Journal of Pharmaceutical Sciences,* 77; 285 (1988), H. Bundgaard, et al; *Chem Pharm Bull,* 32692 (1984), N. Kakeya et al and *The Organic Chemistry of Drug Desig and Drug Action*, Chapter 8, pp 352-401, Academic press, Inc., 1992.

Some examples of prodrugs contemplated include acyl esters, sulfonates and phosphonates.

Suitable pharmaceutically acceptable salts of compounds include, but are not limited to, salts of pharmaceutically acceptable inorganic acids such as hydrochloric, sulphuric, phosphoric nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids. Base salts include, but are not limited to, those formed with pharmaceutically acceptable cations, such as sodium, potassium, lithium, calcium, magnesium, ammonium and alkylammonium. Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

The compounds of the invention may be in crystalline form either as the free compounds or as solvates (for example, of water, i.e., hydrates, or of common organic solvents such as alcohols) and it is intended that both forms are within the scope of the present invention. Methods of solvation are generally known within the art, for example recrystallization from a given solvent.

Thus, subjects which may be treated in accordance with the present invention include mammalian subjects: humans, primates, livestock animals (including cows, horses, sheep, pigs and goats), companion animals (including dogs, cats, rabbits, guinea pigs), and captive wild animals. Laboratory animals such as rabbits, mice, rats, guinea pigs and hamsters are also contemplated as they may provide a convenient test system. Non-mammalian species such as birds, amphibians and fish may also be contemplated in certain embodiments of the invention. A subject may also be referred to herein as an individual, patient, animal or recipient.

Subjects for treatment in accordance with the invention are preferably selected on the basis of requiring or seeking said treatment.

The ingenol compounds are administered to the subject in treatment effective amounts. Suitable effective amounts for administration (dosage) and dosing regimens can be determined by the attending physician and may depend on the cosmetic appearance, anatomical location and area of the skin being treated, as well as the age and general health of the subject.

Advantageously, in certain embodiments the ingenol compound active ingredient is administered as a pharmaceutical composition comprising an ingenol compound with one or more pharmaceutically acceptable adjuvants. Thus, the present invention also relates to the use of an ingenol compound or a pharmaceutically acceptable salt, or prodrug thereof in the manufacture of a medicament for treating aged or photo-aged skin.

Medicaments or compositions suitable for use in the invention may contain the ingenol compound in an amount of from about 0.0001% to up to 100% by weight. In certain embodiments, the composition contains the ingenol compound in an amount of from about 0.0001% to up to about 10% by weight, for example about 0.0005, 0.001, 0.0025, 0.005, 0.0075, 0.01, 0.0125, 0.015, 0.02, 0.025, 0.05, 0.075, 0.1, 0.125, 0.15, 0.2 or 0.25% to about 0.5, 1.0, 2.5 or 5.0%. In one embodiment of the invention, the ingenol compound is ingenol-3-angelate present in an amount of about 0.001 to about 1%. In a further embodiment the ingenol compound, for example ingenol-3-angelate, is present in an amount of about 0.005 to about 0.2%. In a further embodiment thereof, the ingenol compound, such as ingenol-3-angelate, may be present in an amount of from 0.005 to 0.1%, such as about 0.01%.

The ingenol compounds may be administered in any suitable form, such as locally, e.g. by topical application to the area requiring treatment, and/or or by injection into the skin. In particular examples of the invention, the ingenol compound is administered by topical application to the area(s) of skin.

The dosage on application will depend on a number of factors that may readily be determined by the skilled person, but may be one or more doses per day, with a course of treatment lasting from several days to several months, or continuously until the desired result is effected. In certain embodiments, the ingenol compound is administered once or twice daily.

In a preferred embodiment of the invention the ingenol compounds are administered, i.e. applied, topically to the area requiring treatment. Any area of skin on the body may be treated in accordance with the invention. In some embodiments, the invention is directed to the treatment of one or more of the face, neck, throat area surrounding the eyes (e.g. under-eye, eye bags and wrinkles and crows feet), upper chest, hands, back, shoulders, scalp and arms, including the forearms. Certain embodiments of the invention contemplate the treatment of photo-aged skin. Advantageously, the treatment is applied to an area of chronologically- and/or photo-aged skin of at least 10 cm$^2$. In further embodiments, the skin which is treated in accordance with the invention is non-diseased skin i.e. does not presently suffer from disease. In an exemplary embodiment areas of the face and/or the neck/throat may be treated in accordance with the invention. The ingenol compounds may be topically applied in any suitable form including solutions, emulsions (oil-in-water, water-in-oil, aerosols or foams), ointments, pastes, lotions, powders, paints, gels (such as PEP005 (ingenol mebutate) Gel, Peplin Inc.), hydrogels, hydrocolloids and creams may be prepared so as to contain liposomes, micelles, and/or microspheres. Alternatively, the ingenol compounds may be presented in the form of an active occlusive dressing, e.g., where the ingenol compound is impregnated or coated on a dressing such as bandages, gauzes, tapes, nets, face masks, adhesive plaster, films, membranes or patches.

The formulation of compositions and dressings contemplated herein is well known to those skilled in the art, see for example, *Remington's Pharmaceutical Sciences*, 18$^{th}$ Edition, Mack Publishing, 1990. Compositions may contain any suitable carriers, diluents or excipients. These include all conventional solvents, dispersion media, fillers, solid carriers, coatings, antifungal and antibacterial agents, viscosity enhancers, film formers, dermal penetration agents, surfactants, isotonic and absorption agents and the like. The carrier for compositions contemplated by the present invention must be pharmaceutically acceptable in the sense of being compatible with the other ingredients of the composition and not injurious to the subject.

Ointments, as is well known in the art of pharmaceutical formulation, are semi-solid preparations that are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, non-irritating and non-sensitizing. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin, and stearic acid. Preferred water-soluble ointment bases are prepared from polyethylene glycols of varying molecular weight.

Creams, also well known in the art, are viscous liquids or semisolid emulsions, either oil-in-water or water-in-oil. Cream bases are water-washable, and contain an oil phase, an emulsifier, and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic, or amphoteric surfactant.

As will be appreciated by those working in the field of pharmaceutical formulation, gels are semisolid, suspension-type systems. Single-phase gels contain gelling agents distributed substantially uniformly throughout the carrier liquid, which is typically aqueous, but also, preferably, contain an alcohol such as isopropyl alcohol, and, optionally, an oil.

Lotions, for delivery of cosmetic agents, are preparations to be applied to the skin surface without friction, and are typically liquid or semi-liquid preparations in which solid particles, including the active agent, are present in a water or alcohol base. Lotions are usually suspensions of solids, and preferably, for the present purpose, comprise a liquid oily emulsion of the oil-in-water type. Generally the insoluble matter in a lotion is finely divided. Lotions will typically contain suspending agents to produce better dispersions as well as compounds useful for localizing and holding active agent in contact with the skin.

Pastes are semi-solid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

In one embodiment of the invention, the ingenol compound may be topically applied in the form of an isopropyl alcohol-based gel. One suitable formulation includes isopropyl alcohol, benzyl alcohol, a cellulose polymer, such as hydroxyethyl cellulose and buffer (e.g., citrate) at a pH<3. In another embodiment of the invention, the ingenol compound can be formulated for topical application in the form of a macrocetyl ether cream, for example containing cetomacrogel emulsifying wax, white soft paraffin and liquid paraffin.

Formulations may also be prepared with liposomes, micelles, and microspheres. Liposomes are microscopic vesicles having a lipid wall comprising a lipid bilayer, and can be used as drug delivery systems herein as well. Generally, liposome formulations are preferred for poorly soluble or insoluble pharmaceutical agents. Liposomal preparations for use in the invention include cationic (positively charged), anionic (negatively charged) and neutral preparations.

Micelles are known in the art to be comprised of surfactant molecules arranged so that their polar headgroups form an outer spherical shell, while the hydrophobic, hydrocarbon chains are oriented towards the center of the sphere, forming a core. Micelles form in an aqueous solution containing surfactant at a high enough concentration so that micelles naturally result. Micelle formulations can be used in conjunction with the present invention either by incorporation into the reservoir of a topical or transdermal delivery system, or into a formulation to be applied to the body surface.

Microspheres, similarly, may be incorporated into the present formulations and drug delivery systems. Like liposomes and micelles, microspheres essentially encapsulate a drug or drug-containing formulation. Microspheres are generally, although not necessarily, formed from synthetic or naturally occurring biocompatible polymers, but may also be comprised of charged lipids such as phospholipids. Preparation of microspheres is well known in the art and described in the pertinent texts and literature.

It will be understood that the invention may also be practiced in conjunction with the use of other forms of anti-aging or anti-photo-aging therapies, including but not limited to, laser resurfacing, chemical peels, topical retinoids, mechanical re-surfacing (e.g. dermabrasion) and photodynamic therapy (PDT) used to treat chronologically-aged or photo-aged skin.

Additional agents to be used in conjunction with the invention may be formulated into a composition or dressing together with the ingenol compound or compounds or they can be administered separately, either sequentially or together.

It will be recognized that although the terms "chronological-aging" and "photo-aging" are used to refer to the cosmetic and/or physiological effects on the skin as a result of the passage of time and exposure UV radiation, respectively, and that in certain embodiments the subject may be an adult of at least, 20, 30, 40, 50 or 60 years of age, the invention is not to be restricted to adult patients and the ingenol compound or composition comprising said compound may be applied to babies, children or teenagers as appropriate.

Whilst advantageously contemplated for use in the treatment of human aged skin, the ingenol compounds described herein may also be presented for use in veterinary compositions. These may be prepared by any suitable means known in the art. Examples of such compositions include those adapted for topical application e.g. creams, ointments, gels, lotions etc as described above.

The ingenol compounds, for example ingenol-3-angelate or a pharmaceutically acceptable salt thereof, may induce endogenous hyaluronan synthesis in the skin of a subject. Advantageously, the synthesis of high molecular weight hyaluronan is induced. The assessment of induced endogenous hyaluronan may advantageously provide a test or evaluation means for the efficacy of the ingenol compounds.

In a typical example, skin biopsies (4-6 mm punch biopsies) are fixed in 10% buffered formalin and embedded in paraffin. Slides, created from the paraffin blocks, are de-waxed and rehydrated through a series of xylol and graded alcohols. Endogenous peroxidase is blocked by immersing the slides in hydrogen peroxide in methanol for 30 min. For the histochemical detection of HA, a biotinylated hyaluronan-binding protein (bHABP) derived from bovine cartilage (Seikagaku Ltd, Tokyo, Japan) is used. Slides are incubated overnight at 4° C. with bHABP in phosphate-buffered saline (PBS) and bovine serum albumin. After washing with PBS, all samples are incubated with goat serum to block non-specific binding sites. After washing in PBS, sections are incubated at room temperature with avidin-biotin-peroxidase complex (Immunopure ABC peroxidase staining kit, Pierce, Rockford, Ill., USA). The reaction is visualized using 3,3'-diaminobenzidine (DAB, Sigma-Aldrich) and hydrogen peroxide in PBS, at room temperature. The slides are counterstained with Mayer's haematoxylin for 30 s, washed, dehydrated and mounted. Further, protocols are described in the art (see, for example, Bertheim, U. and Hellström, S., 1994; Bertheim, U., et al., 2004; Asari, A., et al., 1992 and Zanna G., et al., 2008).

Using a chaotropic buffer (such as guanidinium chloride), the dermal extracellular matric (ECM) can be extracted from the skin biopsy. The hyaluronan can then be purified from the ECM by anion exchange chromatography and the molecular weight can be determined using gel filtration chromatography against known standards (see, for example, Simpson et al., 2009).

The invention will now be described with reference to the following Examples which are included for the purpose of illustrating certain embodiments of the invention and are not to be considered as limiting the generality hereinbefore described.

EXAMPLES

As used throughout, the term "PEP005" refers to and is interchangeable with ingenol-3-angelate 1. Materials and Methods 1.1 Non-Clinical 1.1.1 Dermal Fibroblast Cell Culture A normal adult skin biopsy (6 mm) was obtained (n=1), with informed consent, from an individual attending the Oral Surgery Clinic, School of Dentistry, Wales College of Medicine, Cardiff. Following the application of a local anaesthetic, the dermal biopsy was collected and adult dermal fibroblast cultures established by single cell suspension technique, following enzymic degradation of the specimen. This technique has previously been reliably used to establish viable primary cultures of both oral and dermal fibroblasts in vitro (Cook et al, 2000; Stephens et al, 2001; 2003). Dermal fibroblasts were cultured in Fibroblast-Serum Containing Medium, containing Dulbecco's Modified Eagle's Medium (DMEM), supplemented with L-glutamine (2 mM), antibiotics (100 U/ml) penicillin G sodium, 100 mg/ml streptomycin sulphate and 0.25 µg/ml amphotericin B) and 10% foetal calf serum (all purchased from Invitrogen Ltd., Paisley, U.K.). Dermal fibroblast cultures were maintained at 37° C., in a 5% $CO_2$/95% air atmosphere, with the culture medium being changed every 2-3 days. Dermal fibroblasts were used between) passage 7-17, for all experiments.

1.1.2 Preparation of PEP005

PEP005, obtained from Peplin in 20 mg batches, was stored at 4° C. When required, the PEP005 was solubilized in dimethyl sulphoxide (DMSO, >99.9%, Sigma Chemical Company, Dorset, U.K.), at a concentration of 10 mg/ml. The solution was mixed for 5 min or until the solution was clear and the PEP005/DMSO stock solution stored at 4° C., where stable for several months. Prior to use, the PEP005/DMSO stock solution was removed from 4° C. storage and warmed to room temperature. The required volumes of PEP005/DMSO were aliquoted into a poly-propylene vessel and the PEP005/DMSO diluted to the required concentration (typically 0.01 µg/ml, 0.1 µg/ml, 1 µg/ml, 10 µg/ml and 100 µg/ml) in Fibroblast-Serum Containing Medium (for dermal fibroblast cultures, Section 3.1), with fresh PEP005/culture medium solutions being prepared daily, at the various concentrations above, due to solution stability. Prior to discarding PEP005/culture medium solutions, at least two volumes of 0.1% sodium hydroxide (Sigma Chemical Company), in 95% ethanol/5% methanol (both from Thermo Fisher Scientific, Leicestershire, U.K.), was added to each solution, to deactivate.

1.1.3 Assessment of Hyaluronan Synthesis by Dermal Fibroblasts

Following trypsinization, dermal fibroblasts were seeded in 24-well tissue culture plates in PEP005-free, Fibroblast-Serum Containing Medium (1 ml), at a cell density of $2.5 \times 10^4$ cell/well. Dermal fibroblasts were maintained at 37° C., in a 5% $CO_2$/95% air atmosphere, for 48 h, prior to maintenance in serum-free, Fibroblast-Serum Containing Medium (1 ml), for a further 48 h. At this stage, the serum-free, culture medium was replaced with Fibroblast-Serum Containing Medium (600 µl), containing 0 µg/ml, 0.01 µg/ml, 0.1 µg/ml, 1 µg/ml, 10 µg/ml or 100 µg/ml PEP005, +/−TGF-$\beta_1$ (10 ng/ml) (three culture wells per PEP005 concentration). A control was also established, consisting of cells in serum-free, Fibroblast-Serum Containing Medium, containing 1% DMSO. The dermal fibroblasts were maintained at 37° C., in a 5% $CO_2$/95% air atmosphere, for 24 h or 72 h, prior to culture medium removal. Hyaluronan synthesis in the collected culture media was quantified, using a Hyaluronic Acid Quantitative Test Kit (Corgenix U.K. Ltd., Cambridgeshire, U.K.), which utilizes a naturally occurring bovine binding protein to hyaluronan. Supernatants were assayed, as per manufacturer's instructions, and optical density measured using a spectrophotometer at 450 nm. Hyaluronan concentrations were determined by comparing the absorbance of the sample against a reference curve prepared from the reagent blank and standards. Each experiment was performed on three separate occasions.

1.1.4 Assessment of Hyaluronan Pericellular Coat Formation by Dermal Fibroblasts Following trypsinization, dermal fibroblasts were seeded in 53 mm bacteriological grade culture dishes (VWR International Ltd., Leicestershire, U.K.), in PEP005-free, Fibroblast-Serum Containing Medium (2 ml), at a density of $7 \times 10^4$ cell/dish. Dermal fibroblasts were maintained at 37° C., in a 5% $CO_2$/95% air atmosphere, overnight, prior to washing in PBS (2×2 ml) and maintenance in serum-free, Fibroblast-Serum Containing Medium (2 ml), containing 0 µg/ml, 0.01 µg/ml, 0.1 µg/ml, 1 µg/ml, 10 µg/ml or 100 µg/ml PEP005, +/−TGF-$\beta_1$ (10 ng/ml) (three culture dishes per PEP005 concentration). A control was also established, consisting of cells in serum-free, Fibroblast-Serum Containing Medium, containing 1% DMSO. The dermal fibroblasts were maintained at 37° C., in a 5% $CO_2$/95% air atmosphere, for 24 h or 72 h. At 24 h and 72 h, the culture dishes were treated with formalized horse blood erythrocytes (TCS Biosciences Ltd., Buckinghamshire, U.K.). The formalized horse blood erythrocytes were washed in PBS, to remove sodium azide (3×20 ml) and centrifuged at 100 g/7 min, at 4° C. The erythrocyte cell pellet obtained was re-suspended in serum-free, Fibroblast-Serum Containing Medium, to a density of $1 \times 10^8$ cells/ml. Aliquots of the erythrocyte cell suspension (500 µl) were supplemented to each culture dish and the dishes agitated, prior to maintenance at 37° C., in a 5% $CO_2$/95% air atmosphere, for 15 min. Zones of erythrocyte exclusion were visualized by light microscopy, using a Zeiss Axiovery 135 Inverted Microscope (Carl Zeiss Ltd., Hertfordshire, U.K.), with a Hamamatsun C5985 chilled CCD camera (Hamamatsu Photonics U.K. Ltd., Hertfordshire, U.K.) and using Openlab Software 3.0.8 (Improvision Ltd., Warwickshire, U.K.). Each experiment was performed on three separate occasions.

1.1.5 Assessment of Hyaluronan Synthase (HAS) Gene Expression by Dermal Fibroblasts Following trypsinization, dermal fibroblasts were seeded in 24-well tissue culture plates, in PEP005-free, Fibroblast-Serum Containing Medium (1 ml), at a cell density of $2.5 \times 10^4$ cell/well. Dermal fibroblasts were maintained at 37° C., in a 5% $CO_2$/95% air atmosphere, overnight. At this stage, the culture medium was replaced with Fibroblast-Serum Containing Medium (600 µl), containing 0 µg/ml, 0.01 µg/ml, 0.1 µg/ml, 1 µg/ml, 10 µg/ml or 100 µg/ml PEP005, +/−TGF-$\beta_1$ (10 ng/ml) (three culture wells per PEP005 concentration). A control was also established, consisting of cells in Fibroblast-Serum Containing Medium, containing 1% DMSO. The dermal fibroblasts were maintained at 37° C., in a 5% $CO_2$/95% air atmosphere, for 24 h or 72 h, prior to washing in PBS (3×1 ml) and Trizol® Reagent (250 µl) added to the cells, for 5 min at room temperature, to induce cell lysis. RNA was extracted by the phenol-chloroform method, as described above, while a cDNA library was generated via random hexamer RT, as described above. RNA (1 µg) was added to 100 M random hexamer (1 µl), 5×RT Buffer (4 µl), 2.5 mM Deoxynucleoside Triphosphates (dNTPs, 5 µl), 2 µl DTT and Nuclease-Free Water, were added to the reaction (total volume, 20 µl). To denature the RNA, reaction tubes were placed in a GeneAmp PCR System 9700 (Applied Biosystems, Cheshire, U.K.) and heated for 5 min/95° C., prior to cooling to 4° C. Superscript (1 µl) and RNAsin® Ribonuclease Inhibitor (1 µl, Promega, Hampshire, U.K.) were added to each tube, and the tubes subjected to 30 cycles at 20° C. for 10 min, 42° C. for 1 h and 95° C. for 5 min, prior to storage at 4° C., until required. As a negative control, RT was also performed, with Nuclease-Free Water replacing the RNA sample.

qPCR was performed, as described above, with the probe and primers for HAS1, HAS2 and HAS3 (target genes) and the 18s ribosomal RNA (reference gene), designed and supplied by Applied Biosystems. PCR was performed in a final volume of 20 µl/sample, with each reaction mix consisting of cDNA (1 µl), target gene primers and probe (1 µl), Taqman® FAST Universal PCR Master Mix (10 µl, Applied Biosystems), and Nuclease-Free Water (8 µl). PCR amplification was performed, using an initial cycle of 95° C. for 1 s, followed by 40 cycles of 60° C. for 20 s. A cDNA-free control was also included. Again, the comparative CT method was used for relative quantification of gene expression. Each experiment was performed on three separate occasions.

1.1.6 Assessment of De Novo Hyaluronan Molecular Weight

Hyaluronan molecular weight sizing, following dermal fibroblast synthesis, was performed as previously described (Meran et al, 2008; Simpson et al, 2009). Dermal fibroblasts were seeded in 6-well tissue culture plates, in PEP005-free, Fibroblast-Serum Containing Medium (2 ml), at $1.5 \times 10^5$ cells/well. Dermal fibroblasts were maintained at 37° C., in a 5% $CO_2$/95% air atmosphere, for 48 h, prior to washing in phosphate buffered saline (PBS, 2×2 ml) and maintenance in serum-free, Fibroblast-Serum Containing Medium (2 ml), for a further 48 h. At 48 h, the serum-free, Fibroblast-Serum Containing Medium was replenished with serum-free, Fibroblast-Serum Containing Medium (2 ml), containing 0 µg/ml, 0.01 µg/ml, 0.1 µg/ml, 1 µg/ml, 10 µg/ml or 100 µg/ml PEP005, +/−TGF-$\beta_1$ (10 ng/ml) (three culture wells per PEP005 concentration), in addition to [$^3$H]-glucosamine (20 µCi/ml, G.E. Healthcare). The dermal fibroblasts were maintained at 37° C., in a 5% $CO_2$/95% air atmosphere, for 24 h or 72 h.

At 24 h and 72 h, the culture medium was removed and each well washed in PBS (1×2 ml). The culture medium and PBS washes were pooled (Conditioned Media Extracts, 8 ml) and stored at −20° C., until required. Once required, the Conditioned Media Extracts were thawed, at 4° C., prior to the addition of an equal volume of pronase, solubilized in 100 mM Tris-HCl buffer, pH 8.0, containing 0.05% sodium azide (all Sigma). The pronase-containing, Conditioned Media Extracts, were incubated at 37° C., for 24 h, prior to ion exchange chromatography on DEAE Sephacel® columns (G.E. Healthcare), equilibrated with 8M urea, in 20 mM BisTris buffer, pH 6.0, containing 0.2% Triton X-100 (all Sigma), to remove low molecular weight peptides and unincorporated radiolabel. The radiolabelled hyaluronan in each Extract was eluted through DEAE Sephacel® ion exchange columns, with 8M urea, in 20 mM BisTris buffer, pH 6.0, containing 0.2% Triton X-100 and 0.3M sodium chloride (Sigma). Each separated Extract was divided into two equal amounts and the radiolabelled hyaluronan precipitated with three volumes of potassium acetate (1% in 95% ethanol, both Sigma), in the presence of chondroitin 4-sulphate, heparin and non-radiolabelled, hyaluronan (all Sigma), as co-precipitants, at 4° C./18 h.

On precipitation, the first half of each Extract was resuspended in 4M guanidinium chloride buffer, pH 6.0, containing 50 mM sodium acetate, 0.5% Triton X-100 and 0.05% sodium azide (all Sigma), prior to hyaluronan molecular weight assessment, via a previously calibrated Sephacryl® S-500 column (G.E. Healthcare). The column was calibrated with [3H] glucosamine hydrochloride, Mr 215; [35S] chondroitin sulfate glycosamino-glycans, Mr 25,000; decorin, Mr 100,000 and [35S] versican, Mr 1,300,000. Elution was performed with 4M guanidinium chloride buffer, pH 6.0, containing 50 mM sodium acetate, 0.5% Triton X-100 and 0.05% sodium azide. To confirm that the chromatography profiles obtained were the result of radiolabelled hyaluronan alone, the second half of each Extract was digested with hyaluronidase (200 µl, Streptomyces hyalurolyticus, ICN Pharmaceuticals), in 20 mM sodium acetate buffer, pH 6.0, containing 0.15M sodium chloride and 0.05% sodium azide, at 37° C./18 h. These digested samples, were mixed with an equal volume (200 µl) of 4M guanidinium chloride buffer, pH 6.0, containing 50 mM sodium acetate, 0.5% Triton X-100 and 0.05% sodium azide, followed by Sephacel® S-500 column elution.

Aliquots (20 µl×3) of each Extract fraction were transferred into scintillation vials, followed by the addition of 70% ethanol (600 µl) and liquid scintillant (4 ml). Scintillation vials were vortexed and [$^3$H]-incorporation quantified using a Packard Tri-Carb 1900CA Liquid Scintillation Analyzer (Perkin Elmer), with values obtained being expressed as disintegrations per minute (dpm). To obtain each chromatography profile, the [$^3$H]-activity of both halves of each Extract, were normalized and corrected for dilution, prior to the hyaluronidase-resistant counts, being subtracted. As such, the chromatography profiles only represent the hyaluronidase-sensitive activity in each PEP005-treated (0 µg/ml, 0.01 µg/ml, 0.1 µg/ml, 1 µg/ml, 10 µg/ml, 100 µg/ml), +/−TGF-$\beta_1$ (10 ng/ml), with the data presented as [$^3$H]-activity per fraction, versus fraction number. Each experiment was performed on two separate occasions.

1.2 Clinical 1.2.1 Case Study of the Cosmetic Potential of PEP005 Gel on Human Skin On day 1 (baseline) and following informed consent, a brief medical history and physical exam was conducted to confirm subject eligibility into this study. Medical history was recorded and a brief medical exam was performed. A 50 cm$^2$ area of skin was marked on one side of the face and designated as the treatment area. Baseline photographs using TruVu® and baseline measurements were recorded. PEP005 (ingenol mebutate) Gel, 0.005% (Peplin Inc.) was then applied to the face to cover the 50 cm$^2$ treatment.

The subject returned to the clinic the following day (day 2). Photographs (including Tru Vu®) and measurements were taken of the application area. Skin reactions were collected based on the subjects report and the Investigator observations. A second application of PEP005 Gel, 0.005% was applied to the treatment area.

The subject returned to the clinic on days 8, 15 and 30 for photographs (including TruVu®), measurements and assessment of skin reactions. Physician Global Assessments were completed at visit on day 15 and 30. The Physician Global Assessment used a 7 point scale, −3 to +3; −3=Markedly Worse, −2=Moderately Worse, −1=Slightly Worse, 0=No Change, +1 Slightly Better, +2=Moderately Better and +3=Markedly Better. The subject exited the study at the day 30 visit.

1.2.2 TruVu® Photography

The TruVu® photography system (Johnson & Johnson Consumer Companies, Inc.) captures images of skin using several different light types. The following different light types were used for this study; visible light, parallel polarize light, cross polarized light and UV light. These four different light types have been shown to reveal natural skin look, fine lines and wrinkles, redness and UV ageing. Results are computer generated in arbitrary units ranging from 'none/low' to 'moderate' to 'elevated/high' and are finally represented as bar graphs for fine lines, wrinkles, redness and UV ageing. These data are manually transposed to an integer from '0' (none/low) to '5' (moderate) to '10' (elevated/high) by the physician.

2. Results 2.1 Assessment of Hyaluronan Synthesis by Dermal Fibroblasts

Figure 1B:
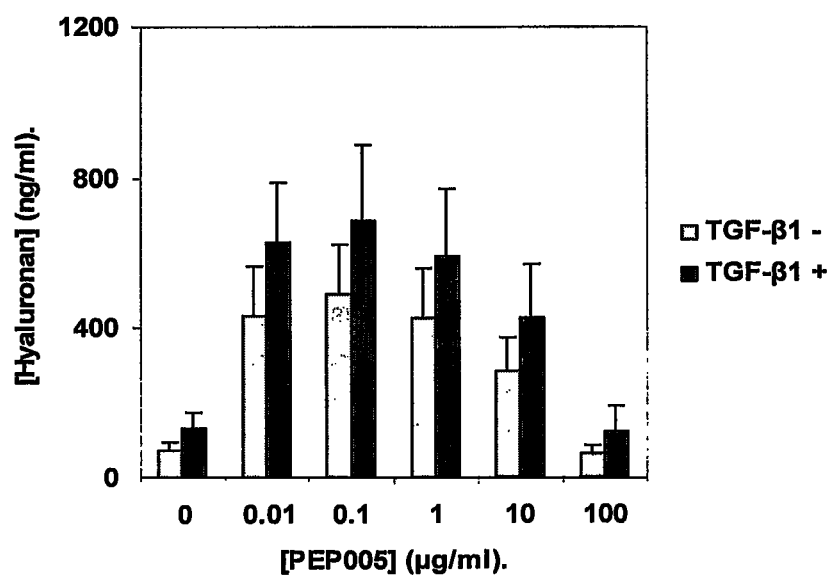

The average values obtained for the quantification of hyaluronan synthesis, by dermal fibroblasts, in the presence of PEP005 (0.01-100 µg/ml), in the absence and presence of TGF-$\beta_1$ (10 ng/ml), at 24 h and 72 h, as quantified using a Hyaluronic Acid Quantitative Test Kit, are shown in FIGS. 1A and 1B, respectively.

The average levels of hyaluronan (ng/ml), synthesized by dermal fibroblasts, at 24 h, in the absence of TGF-$\beta_1$ (10 ng/ml), demonstrated that PEP005 had a significant, stimulatory effect on hyaluronan synthesis, at concentrations of 0.01-10 µg/ml, compared to untreated dermal fibroblast controls (FIG. 1A). The introduction of TGF-$\beta_1$ (10 ng/ml), in the absence of PEP005, induced a slight stimulation of hyaluronan synthesis, at 24 h, while the presence of both PEP005 and TGF-$\beta_1$ (10 ng/ml), appeared to exert a significant, synergistic effect on hyaluronan synthesis, as noted by the enhancement of hyaluronan synthesis, compared to untreated dermal fibroblast controls and to the dermal fibroblasts, in the presence of PEP005 (0.01-100 µg/ml), but in the absence of TGF-$\beta_1$ (10 ng/ml, FIG. 1A).

As at 24 h, the average levels of hyaluronan (ng/ml), synthesized by dermal fibroblasts, at 72 h, in the absence of TGF-$\beta_1$ (10 ng/ml), demonstrated that PEP005 continued to exert a significant, stimulatory effect on hyaluronan synthesis, at concentrations of 0.01-100 µg/ml, compared to untreated dermal fibroblast controls (FIG. 1B).

The effects of PEP005 on hyaluronan synthesis, at all concentrations (0.01-100 µg/ml), were further demonstrated to be solely due to PEP005 alone, and not to the DMSO used for PEP005 solubilization, as dermal fibroblast cultures in the presence of 1% DMSO, exhibited no significant differences in hyaluronan synthesis, compared to untreated dermal fibroblast controls (p>0.05, data not shown).

2.2 Assessment of Hyaluronan Pericellular Coat Formation by Dermal Fibroblasts

Figure 2:
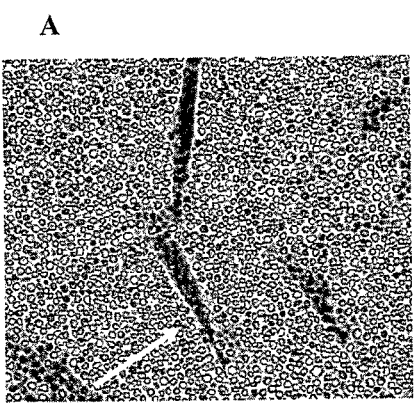
FIG. 2 depicts presentative digital images, obtained for hyaluronan pericellular coat formation, by dermal fibroblasts, cultured in (A) 0, (B) 0.01 µg/ml, (C) 0.1 µg/ml, (D) 1 µg/ml, (E) 10 µg/ml and (F) 100 µg/ml PEP005, in the absence of TGF-$\beta_1$ (10 ng/ml), at 24 h (×200).
Figure 2:
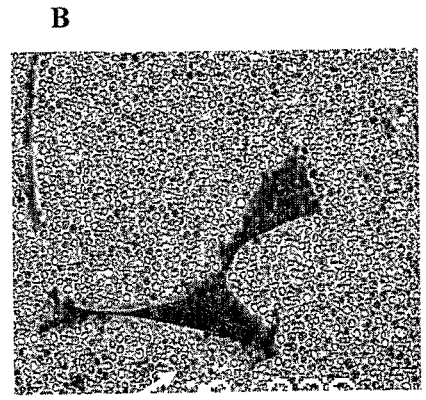
Figure 2:
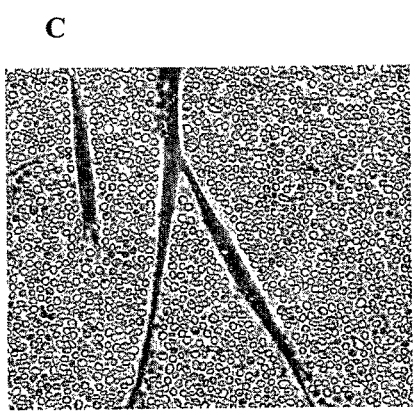
Figure 2:
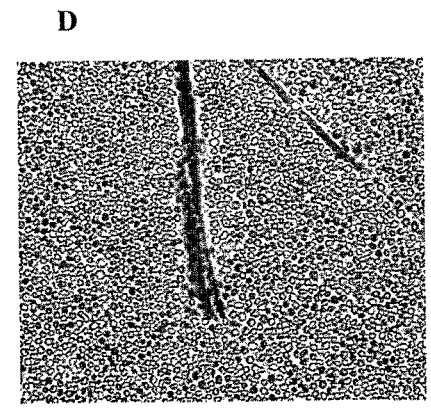
Figure 2:
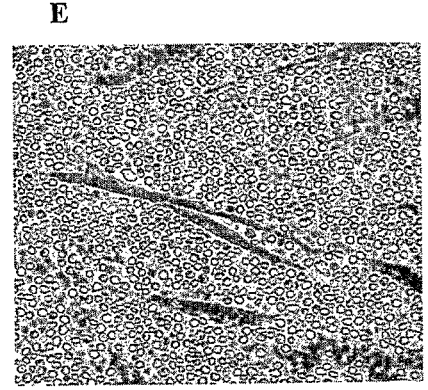
Figure 2:
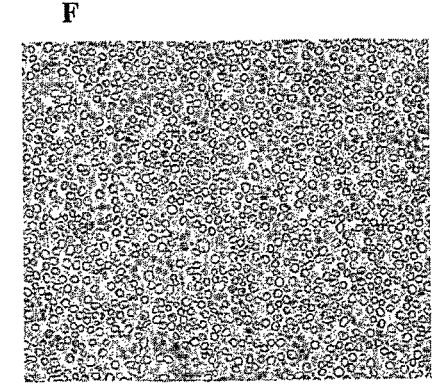
Figure 3:
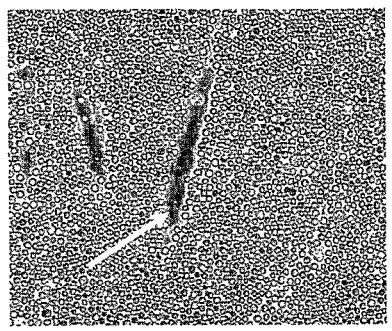
FIG. 3 depicts representative digital images, obtained for hyaluronan pericellular coat formation, by dermal fibroblasts, cultured in (A) 0, (B) 0.01 µg/ml, (C) 0.1 µg/ml, (D) 1 µg/ml, (E) 10 µg/ml and (F) 100 µg/ml PEP005, in the absence of TGF-$\beta_1$ (10 ng/ml), at 72 h (×200).
Figure 3:
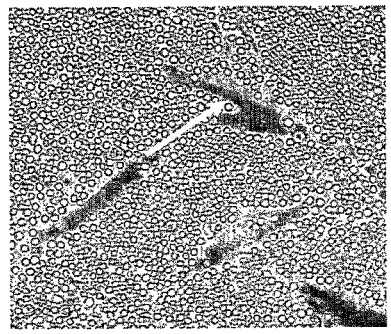
Figure 3:
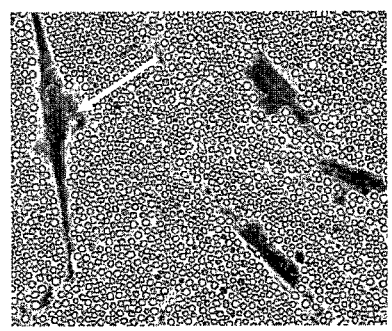
Figure 3:
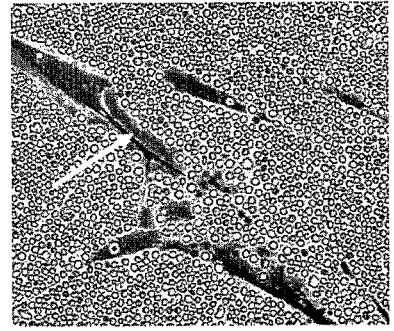
Figure 3:
Figure 3:
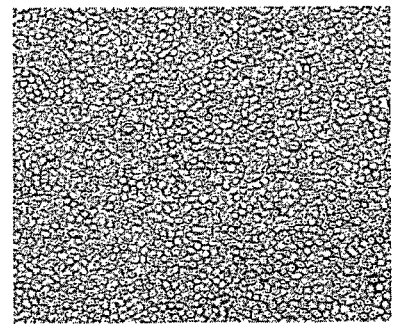

Representative digital images obtained for hyaluronan pericellular coat formation, by dermal fibroblasts, in the presence of PEP005 (0.01-100 µg/ml), in the absence of TGF-$\beta_1$, at 24 h and 72 h, as determined using a particle exclusion assay, are shown in FIGS. 2 and 3, respectively. Representative digital images obtained for hyaluronan pericellular coat formation, by dermal fibroblasts, in the presence of PEP005 (0.01-100 µg/ml) and TGF-$\beta_1$ (10 ng/ml), at 24 h and 72 h, are shown in FIGS. 4 and 5, respectively.

Overall, analysis of hyaluronan pericellular coat formation, at 24 h, in the absence of TGF-$\beta_1$ (10 ng/ml), revealed that there was little pericellular coat formation, by 24 h, in either the PEP005-free control or in PEP005-treated cultures (arrowed, FIG. 2). In contrast, at 72 h, PEP005 appeared to increase pericellular coat size in PEP005-treated samples, at concentrations of 0.01-10 µg/ml, compared to PEP005-free controls (arrowed, FIG. 3). Additionally, morphological changes in the PEP005-treated (0.01-10 µg/ml) fibroblast were consistent with the presence of myofibroblasts, due to fibroblast differentiation.

Figure 4:
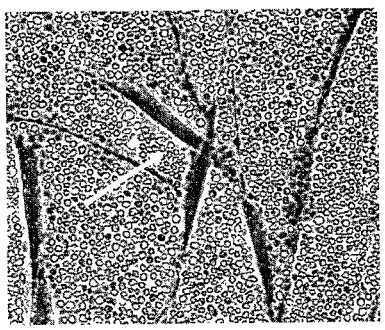
FIG. 4 depicts representative digital images, obtained for hyaluronan pericellular coat formation, by dermal fibroblasts, cultured in (A) 0, (B) 0.01 µg/ml, (C) 0.1 µg/ml, (D) 1 µg/ml, (E) 10 µg/ml and (F) 100 µg/ml PEP005, in the presence of TGF-$\beta_1$ (10 ng/ml), at 24 h (×200).
Figure 4:
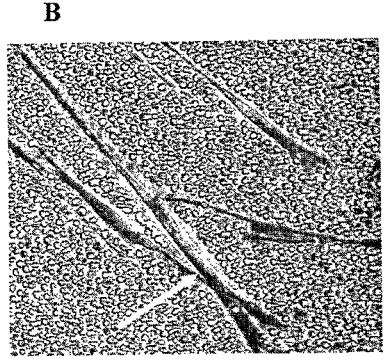
Figure 4:
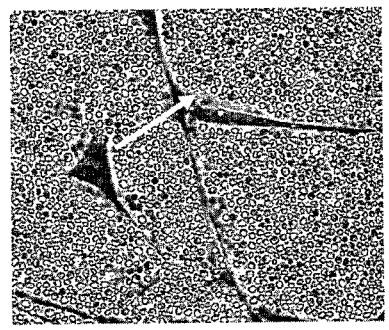
Figure 4:
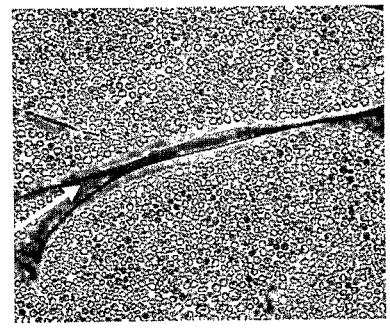
Figure 4:
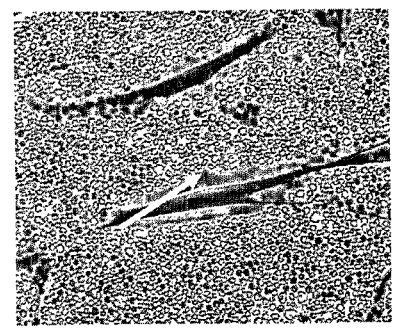
Figure 4:
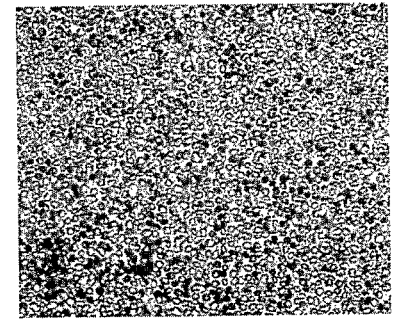

The introduction of TGF-$\beta_1$ (10 ng/ml), in the absence of PEP005, induced a slight increase in hyaluronan pericellular coat formation, at 24 h, while the presence of both PEP005 and TGF-$\beta_1$ (10 ng/ml), appeared to exert a major synergistic effect on hyaluronan pericellular coat formation, evident by the dramatic enhancement of pericellular coat formation (due to hyaluronan accumulation), at 24 h, compared to untreated dermal fibroblast controls and to the dermal fibroblasts, in the presence of PEP005 (0.01-10 µg/ml), but in the absence of TGF-$\beta_1$ (10 ng/ml, arrowed, FIG. 4).

Figure 5:
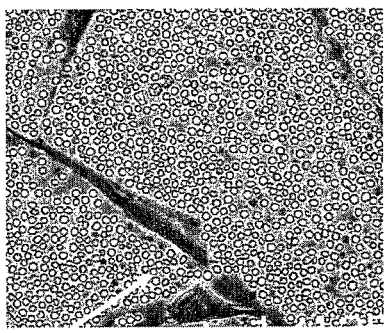
FIG. 5 depicts representative digital images, obtained for hyaluronan pericellular coat formation, by dermal fibroblasts, cultured in (A) 0, (B) 0.01 µg/ml, (C) 0.1 µg/ml, (D) 1 µg/ml, (E) 10 µg/ml and (F) 100 µg/ml PEP005, in the presence of TGF-$\beta_1$ (10 ng/ml), at 72 h (×200).
Figure 5:
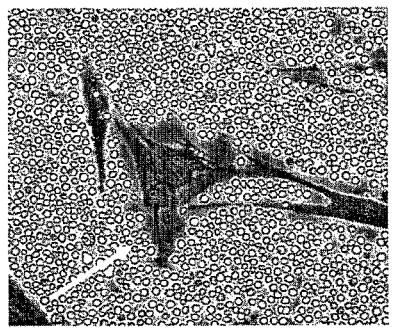
Figure 5:
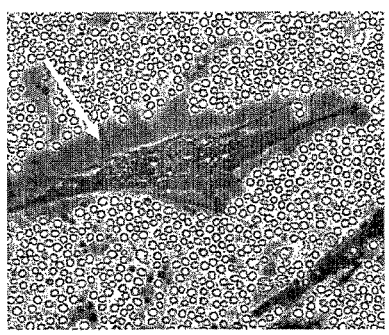
Figure 5:
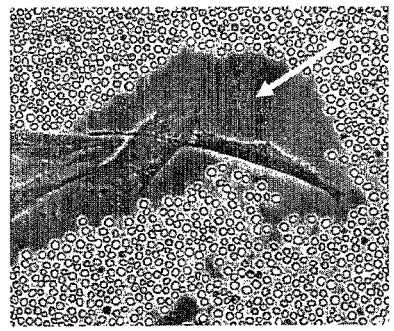
Figure 5:
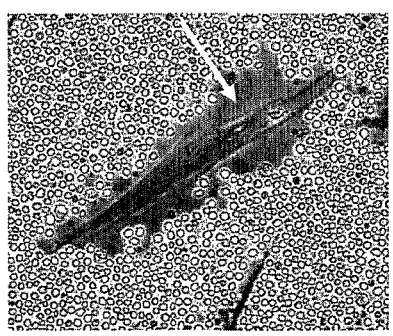
Figure 5:
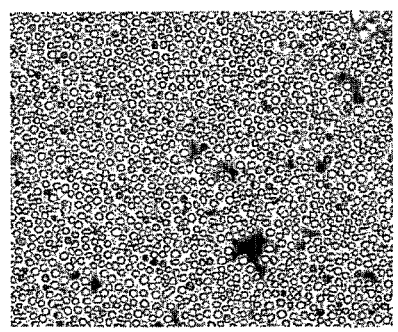

The enhanced hyaluronan pericellular coat formation, at 24 h, in the presence of both PEP005 and TGF-$\beta_1$ (10 ng/ml), was even further enhanced at 72 h, at PEP005 concentrations of 0.01-10 µg/ml, compared to PEP005-free controls (arrowed, FIG. 5). The major changes in cellular morphology evident were consistent with the presence of myofibroblasts.

The effects of PEP005 on hyaluronan pericellular coat formation, at all concentrations (0.01-100 µg/ml), were further demonstrated to be solely due to PEP005 alone, and not to the DMSO used for PEP005 solubilisation, as dermal fibroblast cultures in the presence of 1% DMSO, exhibited no obvious differences in hyaluronan pericellular coat formation, compared to untreated dermal fibroblast controls (data not shown).

Figure 6:
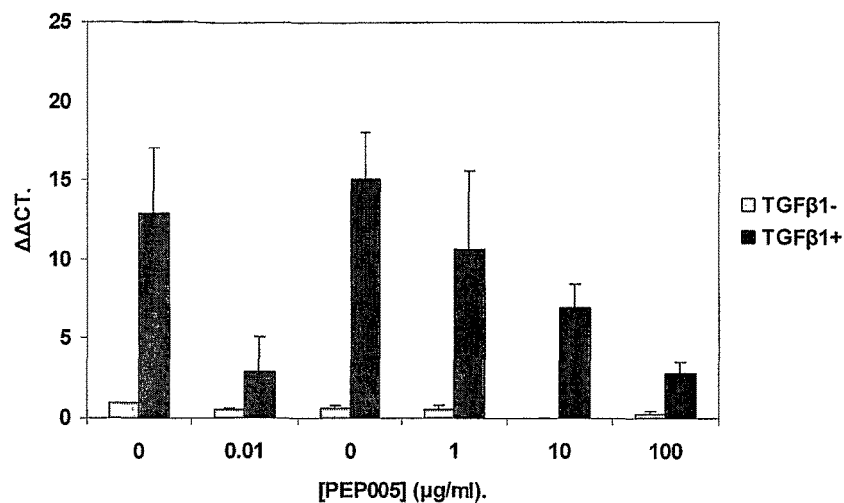
FIG. 6 depicts average HAS1 gene expression, by dermal fibroblasts, cultured in 0 µg/ml, 0.01 µg/ml, 0.1 µg/ml, 1 µg/ml, 10 µg/ml or 100 µg/ml PEP005, in the absence and presence of TGF-$\beta_1$ (10 ng/ml), for (A) 24 h and (B) 72 h (N=2, average±SE, *p<0.05, **p<0.01, compared to PEP005-free, dermal fibroblast controls).
Figure 6:
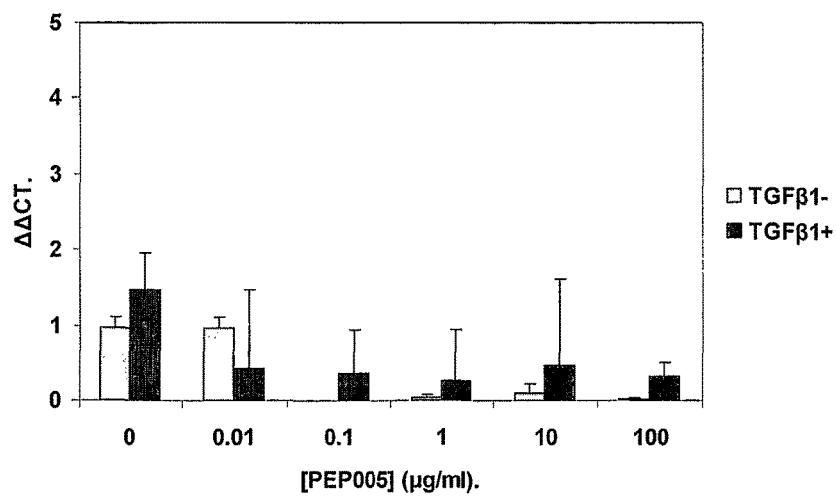
Figure 7:
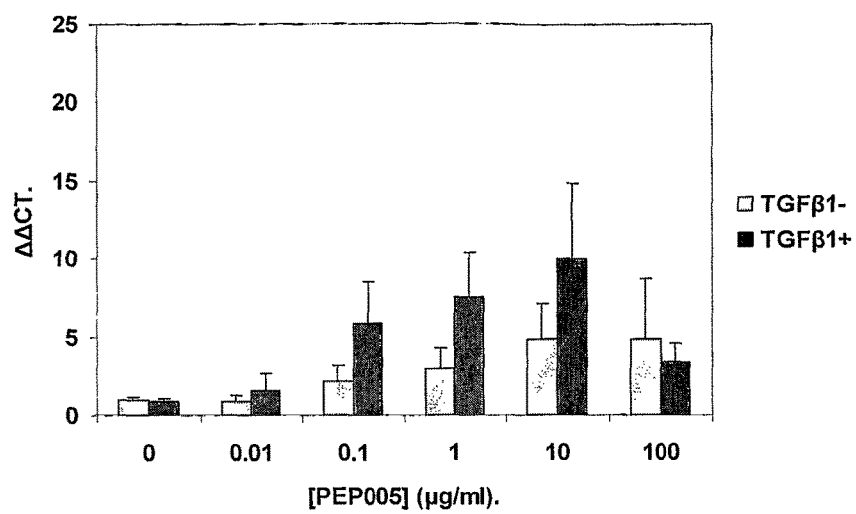
FIG. 7 depicts average HAS2 gene expression, by dermal fibroblasts, cultured in 0 µg/ml, 0.01 µg/ml, 0.1 µg/ml, 1 µg/ml, 10 µg/ml or 100 µg/ml PEP005, in the absence and presence of TGF-$\beta_1$ (10 ng/ml), for (A) 24 h and (B) 72 h (N=3, average±SE).
Figure 7:
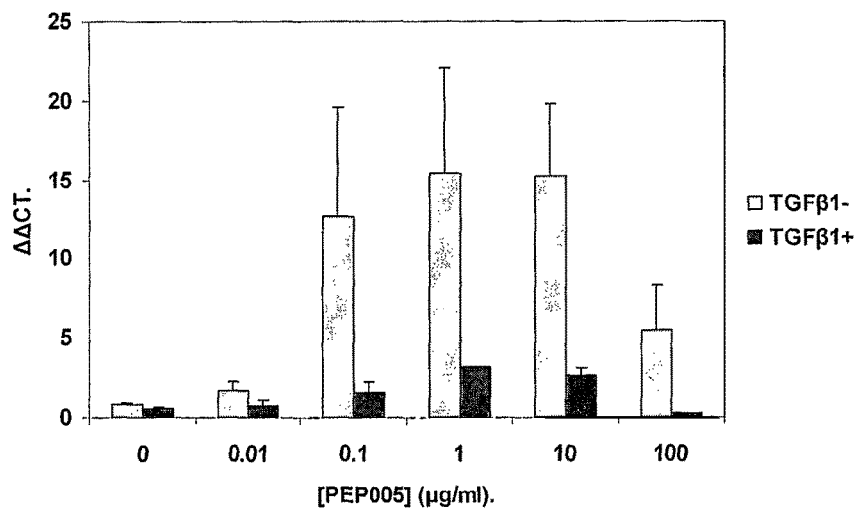
Figure 8:
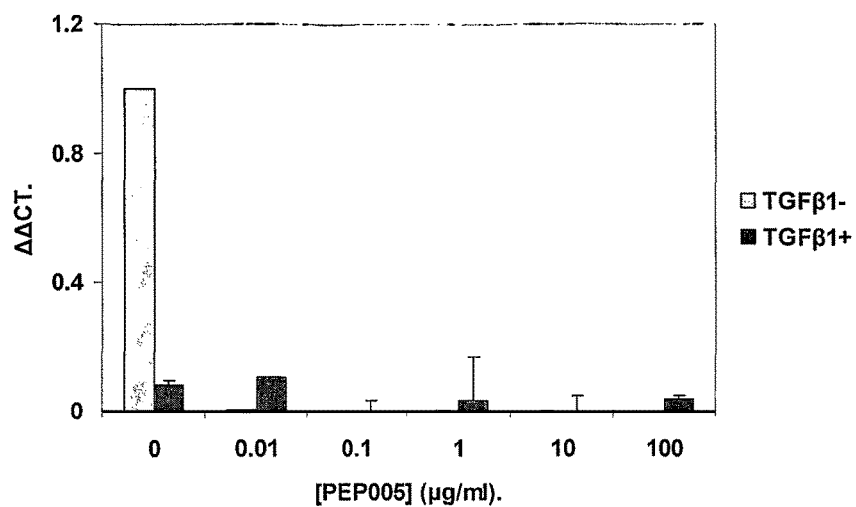
FIG. 8 depicts average HAS3 gene expression, by dermal fibroblasts, cultured in 0 µg/ml, 0.01 µg/ml, 0.1 µg/ml, 1 µg/ml, 10 µg/ml or 100 µg/ml PEP005, in the absence and presence of TGF-$\beta_1$ (10 ng/ml), for (A) 24 h and (B) 72 h (N=3, average±SE).
Figure 8:
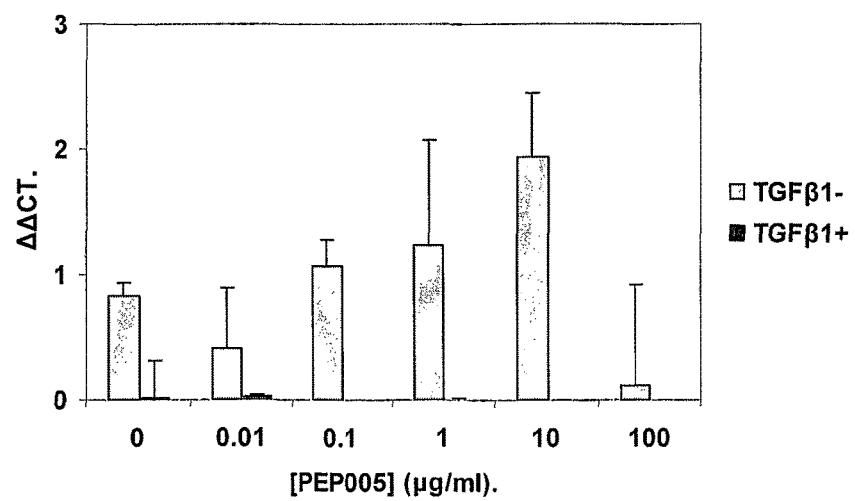
Figure 9:
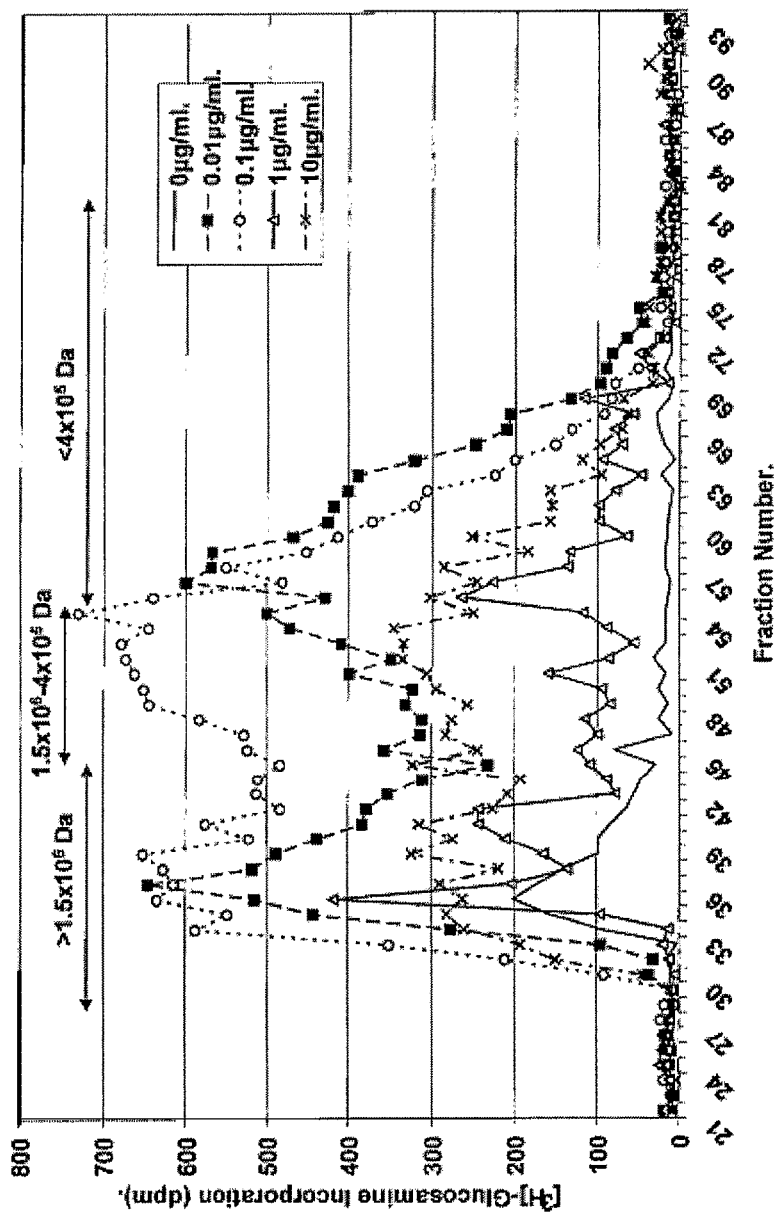
FIG. 9 depicts [3H]-Glucosamine incorporation (at Day 1) of dermal fibroblasts treated with 0, 0.01, 0.1, 1.0 and 10 µg/ml PEP005 in the absence of TGF-$\beta_1$.
Figure 10:
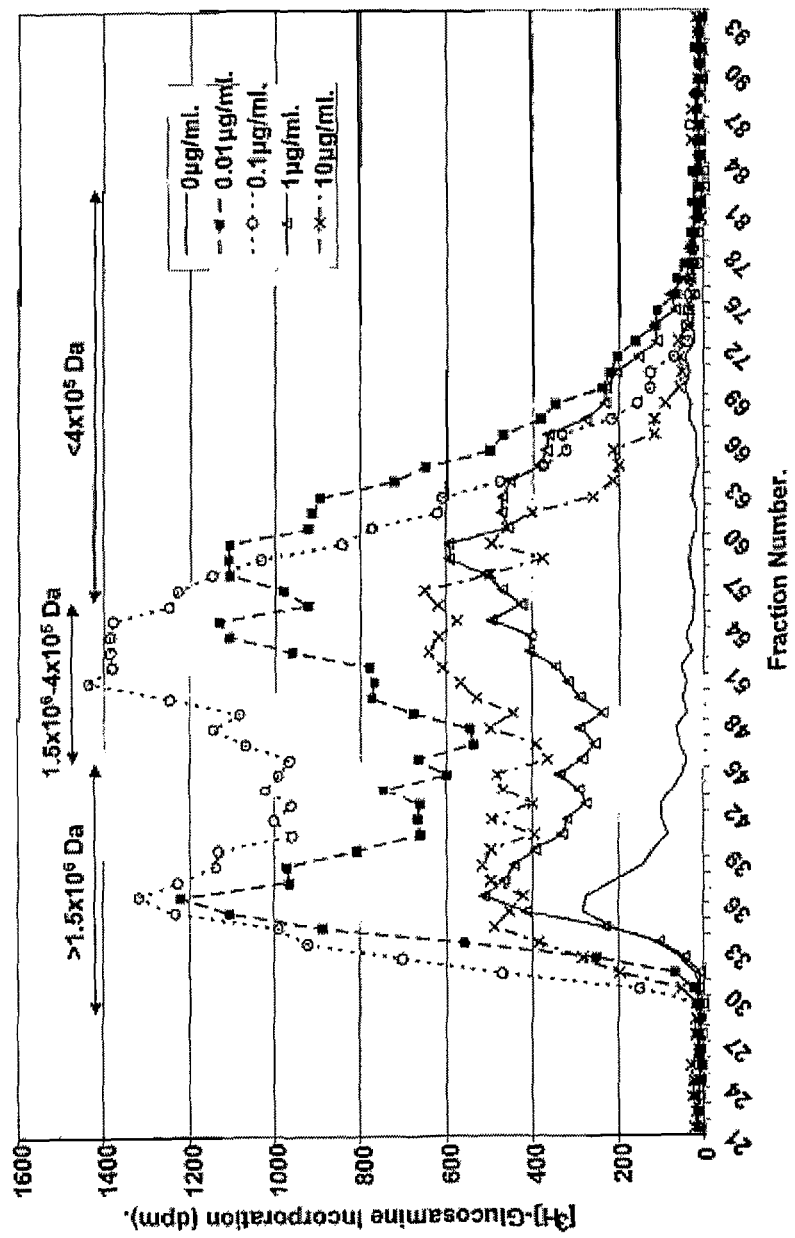
FIG. 10 depicts [3H]-Glucosamine incorporation (at Day 3) of dermal fibroblasts treated with 0, 0.01, 0.1, 1.0 and 10 µg/ml PEP005 in the absence of TGF-$\beta_1$.
Figure 11:
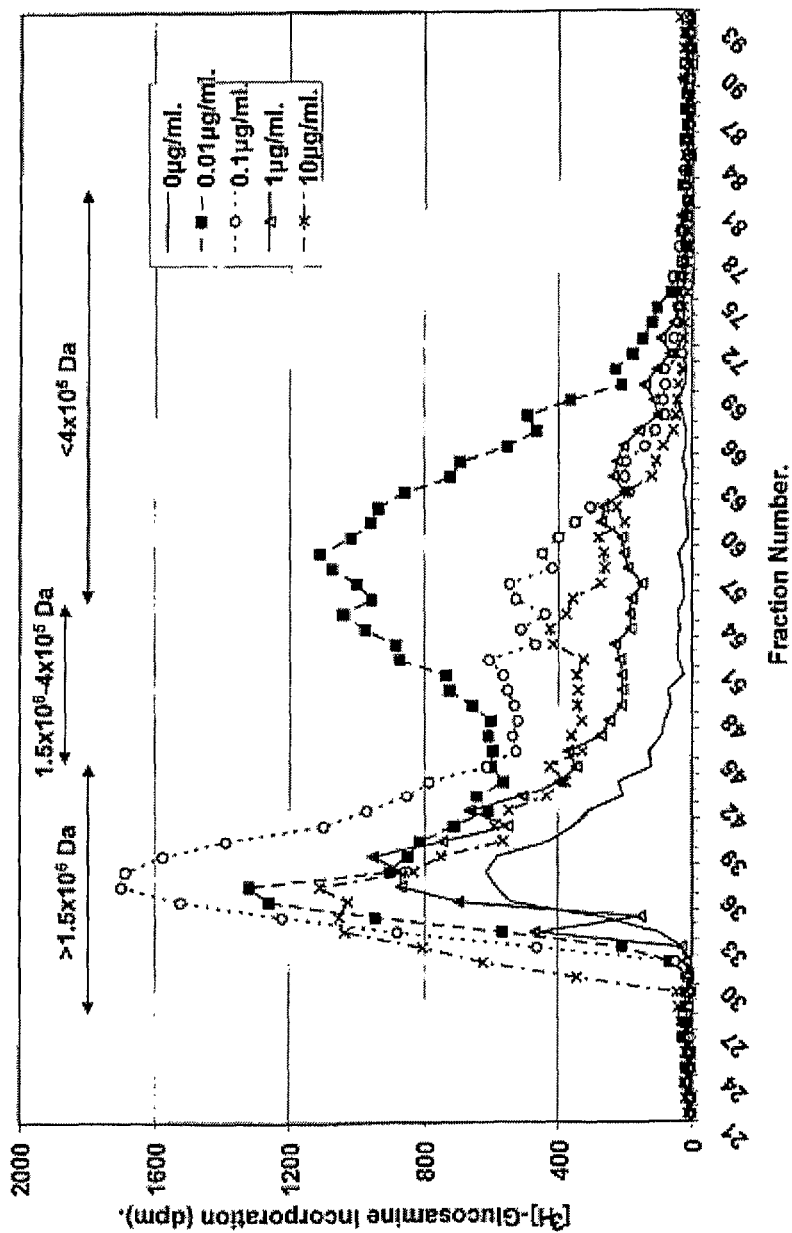
FIG. 11 depicts [3H]-Glucosamine incorporation (at Day 1) of dermal fibroblasts treated with 0, 0.01, 0.1, 1.0 and 10 µg/ml PEP005 in the presence of TGF-$\beta_1$.
Figure 12:
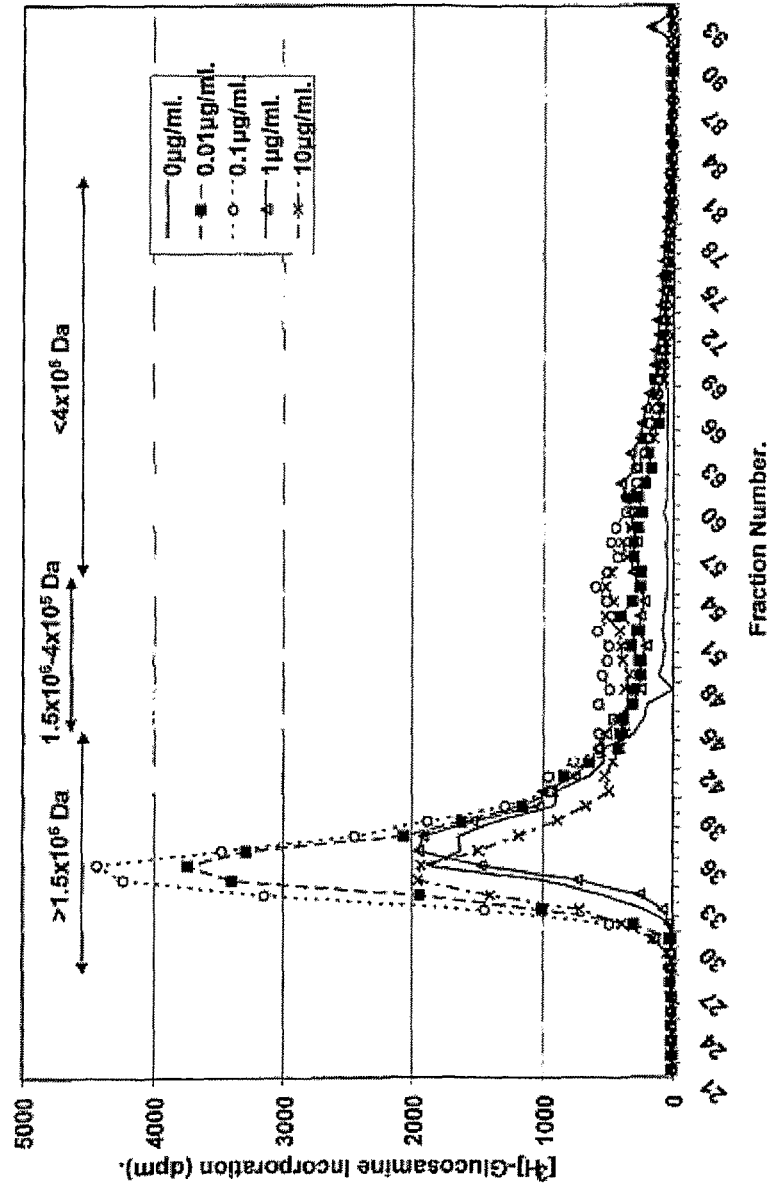
FIG. 12 depicts [3H]-Glucosamine incorporation (at Day 3) of dermal fibroblasts treated with 0, 0.01, 0.1, 1.0 and 10 µg/ml PEP005 in the presence of TGF-$\beta_1$.

2.3 Assessment of Hyaluronan Synthase (HAS) Gene Expression by Dermal Fibroblasts The average values obtained for expression of HAS1, HAS2 and HAS3, by dermal fibroblasts, in the presence of PEP005 (0.01-100 µg/ml), in the absence and presence of TGF-$\beta_1$ (10 ng/ml), at 24 h and 72 h, as quantified by qPCR, are shown in FIGS. 6, 7 and 8, respectively.

The average $\Delta\Delta CT$ values obtained for HAS1, demonstrated that HAS1 expression by dermal fibroblasts, at 24 h, in the absence of TGF-$\beta_1$ (10 ng/ml), was extremely low ($\Delta\Delta CT<0.5$, FIG. 6). Therefore, as virtually no HAS1 expression was evident, PEP005 induced no obvious effects on HAS1 expression, in the absence of TGF-$\beta_1$ (10 ng/ml). In contrast, the introduction of TGF-$\beta_1$ (10 ng/ml), in the absence of PEP005, induced a major up-regulation in HAS1 expression, compared to control dermal fibroblasts (p<0.001, FIG. 6). In the presence of both TGF-$\beta_1$ (10 ng/ml) and PEP005 (0.01-100 µg/ml), a general down-regulation of HAS1 expression (p<0.05 at 0.01 µg/ml, p<0.01 at 100 µg/ml) was observed.

The average ΔΔCT values obtained for HAS1, demonstrated that HAS1 expression by dermal fibroblasts, at 72 h, in the absence of TGF-$\beta_1$ (10 ng/ml), was again relatively low (ΔΔCT<1.0, FIG. 6), so PEP005 induced no obvious effects on HAS2 expression, in the absence of TGF-$\beta_1$ (10 ng/ml). In contrast, the introduction of TGF-$\beta_1$ (10 ng/ml), in the absence of PEP005, again induced an up-regulation in HAS1 expression, compared to control dermal fibroblasts (FIG. 6). In the presence of both TGF-$\beta_1$ (10 ng/ml) and PEP005 (0.01-100 µg/ml), PEP005 induced a general down-regulation in HAS1 expression, at all PEP005 concentrations (0.01-100 µg/ml, FIG. 6). However, the HAS1 gene down-regulation observed with PEP005 and TGF-$\beta_1$ (10 ng/ml), at 72 h, was deemed to be non-significant (p>0.05).

The average ΔΔCT values obtained for HAS2, demonstrated that HAS2 expression by dermal fibroblasts, at 24 h, in the absence of TGF-$\beta_1$ (10 ng/ml), was also relatively low (ΔΔCT<1.0, FIG. 7). It was further demonstrated that PEP005 had a stimulatory effect on HAS2 expression in dermal fibroblasts, at concentrations of 0.1-10 µg/ml, in the absence of TGF-$\beta_1$ (10 ng/ml), compared to untreated dermal fibroblast controls, although the HAS2 gene up-regulation observed with PEP005, at 24 h, was deemed to be non-significant (p>0.05). The introduction of TGF-$\beta_1$ (10 ng/ml), in the absence of PEP005, had little effect on HAS2 expression in dermal fibroblasts, at 24 h, as previously established (Meran et al, 2006, 2007). PEP005 also induced the up-regulation of HAS2 expression in dermal fibroblasts, at concentrations of 0.1-10 µg/ml, in the presence of TGF-$\beta_1$ (10 ng/ml), compared to untreated dermal fibroblast controls. However, the HAS2 gene up-regulation was also deemed to be non-significant (p>0.05).

The average ΔΔCT values obtained for HAS2, demonstrated that HAS2 expression by dermal fibroblasts, at 72 h, in the absence of TGF-$\beta_1$ (10 ng/ml), was again relatively low (ΔΔCT<1.0, FIG. 8). However, PEP005 was demonstrated to stimulate a major up-regulation in HAS2 gene expression at 0.1-10 µg/ml concentrations (FIG. 8). However, the HAS2 gene up-regulation observed at 0.1-10 µg/ml concentrations, was deemed to be non-significant (p>0.05). The introduction of TGF-$\beta_1$ (10 ng/ml), in the absence of PEP005, surprisingly induced minimal effects on HAS2 expression, compared to control dermal fibroblasts (p>0.05, FIG. 8). However, in the presence of both TGF-$\beta_1$ (10 ng/ml) and PEP005 (0.01-100 µg/ml), PEP005 induced a general down-regulation of HAS2 gene expression, at all PEP005 concentrations (0.01-100 µg/ml, FIG. 8). However, the HAS2 gene down-regulation observed with PEP005 and TGF-$\beta_1$ (10 ng/ml), at 72 h, was deemed to be non-significant (p>0.05), compared to PEP005-free, dermal fibroblast controls.

The average ΔΔCT values obtained for HAS3, demonstrated that HAS3 expression by dermal fibroblasts, at 24 h, in the absence of TGF-$\beta_1$ (10 ng/ml), was also relatively low (ΔΔCT<1.0, FIG. 8). It was further demonstrated that PEP005 completely abolished HAS3 expression in dermal fibroblasts, at all PEP005 concentrations (0.01-100 µg/ml), compared to untreated dermal fibroblast controls (FIG. 8), although due to the relatively low levels of HAS3 expression in general, the HAS3 gene down-regulation observed was deemed to be non-significant (p>0.05). The introduction of TGF-$\beta_1$ (10 ng/ml), in the absence of PEP005, also had an inhibitory effect on HAS3 expression in dermal fibroblasts, at 24 h, compared to dermal fibroblasts, in the absence of both PEP005 (0.01-100 µg/ml) and TGF-$\beta_1$ (10 ng/ml) (p<0.01, FIG. 8). PEP005 also induced the down-regulation of HAS3 expression in dermal fibroblasts to barely detectable levels, at concentrations of 0.1-10 µg/ml, in the presence of TGF-$\beta_1$ (10 ng/ml), compared to untreated dermal fibroblast controls. However, the HAS3 gene down-regulation was again deemed to be non-significant at all PEP005 concentrations (0.01-100 µg/ml, p>0.05).

The average ΔΔCT values obtained for HAS3, demonstrated that HAS3 expression by dermal fibroblasts, at 72 h, in the absence of TGF-$\beta_1$ (10 ng/ml), was again relatively low (ΔΔCT<1.0, FIG. 8). However, PEP005 was demonstrated to stimulate the up-regulation in HAS3 gene expression, in the absence of TGF-$\beta_1$ (10 ng/ml), at 1-10 µg/ml concentrations (FIG. 8), to levels greater than the HAS3 gene expression observed at 24 h (FIG. 8). However, the HAS3 gene up-regulation was deemed to be non-significant at these PEP005 concentrations (p>0.05). The introduction of TGF-$\beta_1$ (10 ng/ml), in the absence of PEP005, again had an inhibitory effect on HAS3 expression in dermal fibroblasts, at 72 h, compared to control dermal fibroblasts. Given the virtually negligible levels of HAS3 expression at 72 h, in the presence of TGF-$\beta_1$ (10 ng/ml), PEP005 was demonstrated to exhibit no significant effects on HAS3 expression in dermal fibroblasts (p>0.05), in the presence of TGF-$\beta_1$ (10 ng/ml), at 72 h, at all PEP005 concentrations examined (0.01-100 µg/ml, FIG. 8).

2.5 Assessment of the Affect of PEP005 Gel, 0.005% on Fine Lines, Wrinkles, Redness and UV Ageing Using TruVu® on Human Skin Following two daily applications on days 1 and 2 with PEP005 gel, 0.005% to a 50 cm² area of skin on the face the level of fine lines, wrinkles, redness and UV ageing was assessed at day 30 and compared to levels that were assessed prior to (baseline) application for one subject. It was demonstrated that for this subject the level of fine lines reduced from 10 to 4, wrinkles reduced from 8 to 5, redness was unaffected and UV ageing was reduced from 2 to 1. The Physician Global Assessment for this subject was rated as +2 or moderately better, indicating that globally the two applications of PEP005 Gel, 0.005% resulted in a 'moderately better' overall cosmetic assessment of this subject (in the area of skin treated) at day 30 as compared to baseline (Table 2.5-1).

TABLE 2.5-1

| Skin Condition | Baseline Score | Day 30 |
|---|---|---|
| Fine Lines | 10 | 4 |
| Wrinkles | 8 | 5 |
| Redness | 2 | 2 |
| UV Aging | 2 | 1 |
| Physician Global Assessment | NA | +2 |

2.6 Assessment of De Novo Hyaluronan Molecular Weight

The average values for [3H]-Glucosamine incorporation in the presence of 0, 0.01, 0.1, 1.0 and 10 µg/ml PEP005, in the presence or absence of TGF-$\beta_1$, are presented in FIGS. 9-12.

The hyalruronan synthesized in the presence of PEP005 was predominantly of high (>1.5×10⁶ Da) and medium (<1.5×10⁶-4×10⁵ Da) molecular weight, with the data from day 3 demonstrating further hyaluronan synthesis. It is postulated that medium and low molecular weight hyaluronan observed is due to hyaluronan degradation. The overall extent of hyaluronan degradation is reduced when fibroblasts are incubated in the presence of TGF-$\beta_1$.

REFERENCES

Asari, A., et al., *J. Histochem. Cytochem.*, 1992, 40: 1693-1704
Baumann, L., *J. Pathol.*, 2007, 211: 241-251
Bertheim, U., et al., *British Journal of Plastic Surgery*, 2004, 57: 429-439
Bertheim, U. and Hellström, S., *British Journal of Plastic Surgery*, 1994, 47: 483-489
Cook H. et al., *J Invest Dermatol* 2000; 115: 225-33
Helfrich, Y. R, Sachs, D. L. and Vorhees, J. J, *Dermatology Nursing,* 2008; 20:177-183
Meran, S. et al., *J. Biol. Chem.*, 2007, 282: 25687-25697
Meran, S. et al., *J. Biol. Chem.*, 2008, 283: 6530-6545
Simpson, R. M. et al., *Am. J. Pathol.*, 2009, 175: 1915-1928
Stephens P. et al., *Exp Cell Res* 2003; 283: 22-35
Stephens P. et al., *Br J Dermatol* 2001; 144: 229-237
Stern R., and Maibach, H. I., *Clin. Dermatol.*, 2008, 26: 106-122
Tamino et al., *J. Am. Chem. Soc.*, 2003, 125, 1498-1500
Winkler et al., *J. Am. Chem. Soc.*, 2002, 124, 9726
Zanna, G. et al., *Veterinary Dermatology* 2008, 19: 314-318

The invention claimed is:

1. A method for the treatment of chronologically-aged and/or photo-aged skin in a subject, wherein the chronologically-aged and/or photo-aged skin is free of skin diseases or skin wounds, the method comprising:
topically administering a topical composition to the chronologically-aged and/or photo-aged skin of the subject for improving the cosmetic appearance of the chronologically-aged and/or photo-aged skin, as compared to the cosmetic appearance of the chronologically-aged and/or photo-aged skin of the subject before said topical treatment; the topical composition consisting of ingenol mebutate at a concentration of about 0.01 µg/ml to about 100 µg/ml, one or more pharmaceutically acceptable carriers, and optionally TGF-$\beta_1$.

2. The topical treatment method according to claim 1, wherein the composition is topically administered to an area of the chronologically-aged and/or photo-aged skin that is at least about 10 cm² in size.

3. The topical treatment method according to claim 1, wherein the composition is topically administered to an area of the chronologically-aged and/or photo-aged skin which is selected from the group consisting of the face, the neck, the throat, the areas surrounding the eyes and combinations thereof.

4. The topical treatment method according to claim 1, wherein the composition is topically administered to an area of the chronologically-aged and/or photo-aged skin that is at least about 50 cm² in size.

5. The topical treatment method according to claim 1, wherein the topical composition is an isopropyl alcohol based gel.

6. The topical treatment method according to claim 1, wherein the topical composition is a macrocetyl cream.

7. The topical treatment method according to claim 1, wherein the chronologically-aged and/or photo-aged skin has a skin property selected from the group consisting of dryness, fine lines, wrinkles, furrows, redness, sunspots, irregular pigmentation, UV-aging and combinations thereof.

8. The topical treatment method according to claim 1, wherein the topical treatment method further includes the step of topically applying TGF-$\beta_1$ to the chronologically-aged and/or photo-aged skin.

9. The topical treatment method according to claim 8, wherein the TGF-$\beta_1$ in the further step is topically administered at a concentration of about 10 µg/ml.

10. The topical treatment method according to claim 9, wherein the ingenol mebutate is topically administered to the chronologically-aged and/or photo-aged skin of the subject at a concentration selected from the group consisting of about 0.01 µg/ml, about 0.1 µg/ml, about 10 µg/ml and about 100 µg/ml.

11. A method for the treatment of chronologically-aged and/or photo-aged skin in a subject, wherein the chronologically-aged and/or photo-aged skin is free of skin diseases or skin wounds, said method comprising:
topically administering a topical composition to the chronologically-aged and/or photo-aged skin for improving the cosmetic appearance of the chronologically-aged and/or photo-aged skin of the subject, as compared to the cosmetic appearance of the chronologically-aged and/or photo-aged skin of the subject before said topical treatment; and the topical composition consisting of ingenol mebutate at a dosage strength of from about 0.00001% to about 10% by weight of the topical composition, one or more pharmaceutically acceptable carriers, and optionally TGF-$\beta_1$.

12. The topical treatment method according to claim 11, wherein the topical composition is topically administered at least twice.

13. The topical treatment method according to claim 11, wherein the topical composition is topically administered at least twice on consecutive days.

14. The topical treatment method according to claim 11, wherein the composition is topically administered to an area of the chronologically-aged and/or photo-aged skin at a concentration of about 0.005% by weight.

15. The topical treatment method according to claim 11, wherein the composition is topically administered to an area of the chronologically-aged and/or photo-aged skin that is at least about 10 cm².

16. The topical treatment method according to claim 11, wherein the composition is topically administered to an area of the chronologically-aged and/or photo-aged skin that is at least about 50 cm².

17. The topical treatment method according to claim 11, wherein the composition is topically administered to an area of the chronologically-aged and/or photo-aged skin which is selected from the group consisting of the face, the neck, the throat, the areas surrounding the eyes and combinations thereof.

18. The topical treatment method according to claim 11, wherein said topical treatment method includes the step of inducing endogenous hyaluranon synthesis in dermal fibroblasts of the subject.

19. The topical treatment method according to claim 11, wherein said topical treatment method further includes the step of topically applying TGF-$\beta_1$ to the chronologically-aged and/or photo-aged skin.

20. The topical treatment method according to claim 19, wherein the TGF-$\beta_1$ in the further step is topically administered at a concentration of about 10 µg/ml.

21. A method for the treatment of chronologically-aged and/or photo-aged skin in a subject on the subject's neck or face, wherein the chronologically-aged and/or photo-aged skin is free of skin diseases or skin wounds, said method comprising:

topically administering a topical composition to the chronologically-aged and/or photo-aged skin on the subject's neck or face at least once for improving the cosmetic appearance of one or more of dryness, fine lines, wrinkles, furrows, redness, sunspots, irregular pigmentation and UV-aging on the subject's neck or face, as compared to the cosmetic appearance of the dryness, fine lines, wrinkles, furrows, redness, sunspots, irregular pigmentation or UV-aging before said topical treatment; and the topical composition consisting of ingenol mebutate at a dosage strength of from about 0.00001% to about 10% by weight of the topical composition, one or more pharmaceutically acceptable carriers, and optionally TGF-$\beta_1$.

22. The topical treatment method according to claim 21, wherein the topical composition is topically administered at least twice.

23. The topical treatment method according to claim 21, wherein the topical composition is topically administered at least twice on consecutive days.

24. The topical treatment method according to claim 21, wherein the composition is topically administered to an area of the chronologically-aged and/or photo-aged skin at a concentration of about 0.005% by weight.

25. The topical treatment method according to claim 21, wherein the composition is topically administered to an area of the chronologically-aged and/or photo-aged skin that is at least about 10 cm$^2$ in size.

26. The topical treatment method according to claim 21, wherein the composition is topically administered to an area of the chronologically-aged and/or photo-aged skin that is at least about 50 cm$^2$ in size.

27. The topical treatment method according to claim 21, wherein the composition is topically administered to an area of the chronologically-aged and/or photo-aged skin which is selected from the group consisting of the face, the neck, the throat, the areas surrounding the eyes and combinations thereof.

28. The topical treatment method according to claim 21, wherein said topical treatment method includes the step of inducing endogenous hyaluranon synthesis in dermal fibroblasts of the subject.

29. The topical treatment method according to claim 21, wherein said topical treatment method further includes the step of topically applying TGF-$\beta_1$ to the chronologically-aged and/or photo-aged skin.

30. The topical treatment method according to claim 29, wherein the TGF-$\beta_1$ in the further step is topically administered at a concentration of about 10 μg/ml.

31. A method for inducing endogenous hyaluranon synthesis in chronologically-aged and/or photo-aged skin of a subject, wherein the chronologically-aged and/or photo-aged skin is free of skin diseases or skin wounds, said method comprising:

topically administering at least once a topical composition to the chronologically-aged and/or photo-aged skin of the subject for inducing endogenous hyaluranon synthesis in the chronologically-aged and/or photo-aged skin to improve the cosmetic appearance of the chronologically-aged and/or photo-aged skin, as compared to the cosmetic appearance of the chronologically-aged and/or photo-aged skin of the subject before said topical treatment; and the topical composition consisting of ingenol mebutate at a dosage strength of from about 0.00001% to about 10% by weight of the topical composition, one or more pharmaceutically acceptable carriers, and optionally TGF-$\beta_1$.

32. The topical treatment method according to claim 31, wherein the topical composition is topically administered to the chronologically-aged and/or photo-aged skin at least twice.

33. The topical treatment method according to claim 31, wherein the topical composition is topically administered to the chronologically-aged and/or photo-aged skin at least twice on consecutive days.

34. The topical treatment method according to claim 31, wherein the composition is topically administered to an area of the chronologically-aged and/or photo-aged skin at a concentration of about 0.005% by weight.

35. The topical treatment method according to claim 31, wherein the composition is topically administered to an area of the chronologically-aged and/or photo-aged skin that is at least about 10 cm$^2$ in size.

36. The topical treatment method according to claim 31, wherein the composition is topically administered to an area of the chronologically-aged and/or photo-aged skin that is at least about 50 cm$^2$ in size.

37. The topical treatment method according to claim 31, wherein the composition is topically administered to an area of the chronologically-aged and/or photo-aged skin which is selected from the group consisting of the face, the neck, the throat, the areas surrounding the eyes and combinations thereof.

38. The topical treatment method according to claim 31, wherein the topical treatment method further includes the step of topically applying TGF-$\beta_1$ to the chronologically-aged and/or photo-aged skin to further induce the endogenous hyaluranon synthesis in the dermal fibroblasts.

39. The topical treatment method according to claim 38, wherein the TGF-$\beta_1$ in the further step is topically administered at a concentration of about 10 μg/ml.

* * * * *